US012599657B2

(12) United States Patent
Dahl et al.

(10) Patent No.: US 12,599,657 B2
(45) Date of Patent: *Apr. 14, 2026

(54) ENHANCEMENT OF VACCINE EFFICACY VIA BIOMASS AND/OR RELATED MATERIAL IN ANIMAL DRINK AND FEED

(71) Applicant: ZIVO Bioscience, Inc., Bloomfield Hills, MI (US)

(72) Inventors: Andrew A. Dahl, Bloomfield Hills, MI (US); William P. Pfund, Bloomfield Hills, MI (US); Amy E. Steffek, Bloomfield Hills, MI (US)

(73) Assignee: ZIVO BIOSCIENCE, INC., Bloomfield Hills, MI (US)

( * ) Notice: Subject to any disclaimer, the term of this patent is extended or adjusted under 35 U.S.C. 154(b) by 1185 days.

This patent is subject to a terminal disclaimer.

(21) Appl. No.: 17/367,193

(22) Filed: Jul. 2, 2021

(65) Prior Publication Data

US 2022/0062403 A1     Mar. 3, 2022

Related U.S. Application Data

(60) Provisional application No. 63/047,517, filed on Jul. 2, 2020.

(51) Int. Cl.
| | |
|---|---|
| *A61K 39/02* | (2006.01) |
| *A61K 39/12* | (2006.01) |
| *A61K 39/00* | (2006.01) |

(52) U.S. Cl.
CPC ........ *A61K 39/12* (2013.01); *A61K 2039/545* (2013.01); *A61K 2039/552* (2013.01); *A61K 2039/55572* (2013.01)

(58) Field of Classification Search
None
See application file for complete search history.

(56) References Cited

U.S. PATENT DOCUMENTS

| | | | |
|---|---|---|---|
| 6,066,673 A | 5/2000 | McIver et al. | |
| 7,205,284 B2 | 4/2007 | Pasco et al. | |
| 7,846,452 B2 | 12/2010 | Pasco et al. | |
| 8,563,701 B2 | 10/2013 | Ehmann et al. | |
| 2014/0287919 A1 | 9/2014 | Levine et al. | |

FOREIGN PATENT DOCUMENTS

| | | | |
|---|---|---|---|
| WO | 2008083453 A1 | | 7/2008 |
| WO | WO 0057719 | * | 5/2010 |
| WO | 2015099817 A1 | | 7/2015 |

OTHER PUBLICATIONS

Inagawa et al. (2011PubMed 31(7): 2431-2436).*
Rentea et al. (2012; J Pediatr Surg Jun. 2012;47(6):1135-42.).*

Vantanen et al. (2016; Cell. 165(4): 842-853).*
Benjamin et al. (2016; J. Dairy Sci. 99(7): 5750-5763).*
Nawab et al., "Chicken Toll-Like Receptors and Their Significance in Immune Response and Disease Resistance", International Reviews of Immunology, 2019, vol. 38, No. 6, pp. 284-306, Taylor & Francis Group.
Peek et al., "Coccidiosis in Poultry: Anticoccidial Products, Vaccines and Other Prevention Strategies", 2011, Veterinary Quarterly, vol. 31, No. 3, pp. 143-161, Taylor & Francis Group, LLC.
Pu et al., "Toll-Like Receptor 4 Agonist, Lipopolysaccharide, Increases the Expression Levels of Cytokines and Chemokines in Human Peripheral Blood Mononuclear Cells", Experimental and Therapeutic Medicine, 2014, vol. 8, pp. 1914-1918.
Pugh et al., "The Majority of In Vitro Macrophage Activation Exhibited by Extracts of Some Immune Enhancing Botanicals is Due to Bacterial Lipoproteins and Lipopolysaccharides", International Immunopharmacology, Jul. 2008, vol. 8, No. 7, pp. 1023-1032, NIH Public Access.
Quiroz-Castañeda et al., "Control of Avian Coccidiosis: Future and Present Natural Alternatives", BioMed Research International, 2015, vol. 2015, Article ID 430610, 11 pages, Hindawi Publishing Corporation.
Ritzi et al., "Combination of Probiotics and Coccidosis Vaccine Enhances Protection Against an Eimeria Challenge", Veterinary Research, 2016, vol. 47, No. 111, 8 pages, BioMed Central.
Rosales-Mendoza, "Algae-Based Biopharmaceuticals", eBook, 2016, 172 pages, Springer International Publishing, Switzerland.
Ryšánek, "Terrestrial Algae of the Genus Klebsormidium (Streptophyta) in the Light of the Hypothesis 'Everything is Everywhere, But the Environment Selects'", Ph.D. Thesis, 2016, 199 pages, Charles University in Prague.
Schink et al., "Anti-Inflammatory Effects of Cinnamon Extract and Identification of Active Compounds Influencing the TLR2 and TLR4 Signaling Pathways", Food & Function, 2018, vol. 9, pp. 5950-5964, Royal Society of Chemistry.
Shannon et al., "Antibacterial Derivatives of Marine Algae: An Overview of Pharmacological Mechanisms and Applications", Marine Drugs, 2016, vol. 14, No. 81, 23 pages, MDPI, Basel, Switzerland.
Skjånes et al., "Potential for Green Microalgae to Produce Hydrogen, Pharmaceuticals and Other High Value Products in a Combined Process", Critical Reviews in Biotechnology, 2013, vol. 33, No. 2, pp. 172-215, Informa Healthcare USA, Inc.

(Continued)

*Primary Examiner* — Jennifer E Graser

(57) ABSTRACT

An effective treatment method for a broad variety of diseases in both animals and humans is disclosed. The method includes combining one or more vaccines with a treatment compound to enhance vaccine efficacy. The disclosed treatment compound does not act directly on the pathogen, and thus the organisms cannot readily develop resistance to the treatment. When a compound such as, but not limited to, the disclosed compound is used in conjunction with one or more vaccines, a synergistic effect is realized. The suggested compound is derived from a lipopolysaccharide (LPS) of gram negative bacteria. The treatment compound is combined with one or more appropriate vaccines and is administered early in the life of an animal to achieve a synergistic effect compared with the use of the treatment compound or the vaccine alone.

7 Claims, 11 Drawing Sheets

(56)　　　　　References Cited

OTHER PUBLICATIONS

Spruijt et al., "Opportunities for Micro Algae as Ingredient in Animal Diets", Application Centre for Renewable Resources, Oct. 2016, 48 pages.

Tian et al., "Effects of Dietary Yeast Beta-Glucans Supplementation on Growth Performance, Gut Morphology, Intestinal Clostridium Perfringens Population and Immune Response of Broiler Chickens Challenged with Necrotic Enteritis", Animal Feed Science and Technology, 2016, vol. 215, pp. 144-155, Elsevier B.V.

Tibbetts et al., "Biochemical Characterization of Microalgal Biomass from Freshwater Species Isolated in Alberta, Canada for Animal Feed Applications", Algal Research, 2015, vol. 11, pp. 435-447, Elsevier B.V.

"Toll-Like Receptor Signaling Pathways LTA", 2013, 2 pages, R & D Systems.

"Toll-Like Receptor Signaling Pathways TLR3", 2013, 2 pages, R & D Systems.

"Toll-Like Receptor Signaling Pathways TLR4", 2013, 2 pages, R & D Systems.

"Toll-Like Receptor Signaling Pathways TLR5", 2013, 2 pages, R & D Systems.

"Toll-Like Receptor Signaling Pathways Overview of Toll-Like Receptors", 2013, 2 pages, R & D Systems.

Wang et al., "GABA Regulates the Proliferation and Apoptosis of MAC-T Cells Through the LPS-Induced TLR4 Signaling Pathway", Research in Veterinary Science, 2018, vol. 118, pp. 395-402, Elsevier Ltd.

Yaakob et al., "An Overview: Biomolecules from Microalgae for Animal Feed and Aquaculture", Journal of Biological Research, 2014, vol. 21, No. 6, 10 pages, BioMed Central.

Zhang et al., "Cellular Composition and Differentiation Signaling in Chicken Small Intestinal Epithelium", Animals, 2019, vol. 9, No. 870, 12 pages, MDPI, Basel, Switzerland.

K. Fries-Craft, M. M. Meyer, and E. A. Bobeck, Algae-based feed ingredient protects intestinal health during Elmeria challenge and alters systemic immune responses with differential outcomes observed during acute feed restriction, Department of Animal Science, Iowa State University, Ames, IA 50011, USA, pp. 1-14.

J. Pieniazek, M. P. Williams, R. Latham, H. Walters, T. A. Wickersham, R. Levine, J. Lebrun, D. Caldwell, and J.T. Lee, Evaluation of an Algai Beta-1,3-Glucan on Broiler Growth Performance and Immune Response, Department of Poultry Science, Texas A&M AgriLife Research and Extension, Texas A&M System, College Station, TX, USA; Department of Animal Science, Texas A&M AgriLife Research, College Station TX, USA, Algai Scientific Corporation, Plymouth, MI, USA, pp. 201-210.

R. Levine, G. Horst, R. Tonda, B. Lumpkins and G. Mathis, Evaluation of the effects of feeding dried algae containing beta-1,3-glucan on broilers challenged with Elmeria, Kemin Industries, Des Moines, IA, and Southern Poultry Research, Athens, GA, USA, pp. 3494-3500.

Abbas et al., "Botanicals: An Alternative Approach for the Control of Avian Coccidiosis", Jun. 2012, World's Poultry Science Journal, vol. 68, pp. 203-215, World's Poultry Science Association.

Abbas, Talha E., "Phytogenic Feed Additives as a Coccidiostat in Poultry", Bulletin of Environment, Pharmacology and Life Sciences, Jun. 2012, vol. 1 [7], pp. 22-24, Academy for Environment and Life Sciences, India.

Algal Scientific, "Algamune® Immune Support for Antibiotic Free Production", Brochure, 2015, pp. 1-20, Algal Scientific, Plymouth, Michigan.

Algal Scientific, "Evaluation of Algamune® ZPC on Poultry Performance", Performance Trial, Jan. 2015, pp. 1-8, Algal Scientific, Plymouth, Michigan.

Algal Scientific, Algamune® AM Product Specifications, Nov. 2013, 2 pages, Algal Scientific, Plymouth, Michigan.

Almeida et al., "Differential TLR2 Downstream Signaling Regulates Lipid Metabolism and Cytokine Production Triggered by Mycobacterium Bovis BCG Infection", Bichimica et Biophysica Acta, 2014, pp. 97-107, Elsevier B.V.

Alva-Murillo et al., "Sodium Octanoate Modulates the Innate Immune Response of Bovine Mammary Epithelial Cells Through the TLR2/P38/JNK/ERK1/2 Pathway: Implications During *Staphylococcus aureus* Internalization", Frontiers in Cellular and Infection Microbiology, Mar. 2017, vol. 7, Article 78, pp. 1-15.

Balachandran et al., "Toll-Like Receptor 2-Dependent Activation of Monocytes by Spirulina Polysaccharide and Its Immune Enhancing Action in Mice", International Immunopharmacology, 2006, vol. 6, pp. 808-1814, Elsevier B.V.

Bedick et al., "Innate Immune Reactions Stimulated by a Lipopolysaccharide-Like Component of the Alga Prototheca (Strain 289)", Naturwissenschaften, 2001, vol. 88, pp. 482-485, Springer-Verlag.

Bozkurt et al., "An Update on Approaches to Controlling Coccidia in Poultry Using Botanical Extracts", British Poultry Science, Jan. 2014, vol. 54, Issue 6, pp. 713-727, Taylor & Francis Group.

Caly et al., "Alternatives to Antibiotics to Prevent Necrotic Enteritis in Broiler Chickens: A Microbiologist's Perspective", Frontiers in Microbiology, Dec. 2015, vol. 6, Article 1336, pp. 1-12.

Carillo et al., "Structural Investigation of the Antagonist LPS from the Cyanobacterium Oscillatoria Planktothrix FP1", Carbohydrate Research, 2014, vol. 88, pp. 73-80, Elsevier Ltd.

Cario et al., "Toll-Like Receptor 2 Controls Mucosal Inflammation by Regulating Epithelial Barrier Function", Gastroenterology, 2007, vol. 132, No. 4, pp. 1359-1374, AGA Institute.

Cario, "Barrier-Protective Function of Intestinal Epithelial Toll-Like Receptor 2", Mucosal Immunology, Nov. 2008, vol. 1, Supplement 1, pp. S62-S66, Nature Publishing Group.

Chapman, "Milestones in Avian Coccidiosis Research: A Review", Poultry Science, 2014, vol. 93, pp. 501-511, Poultry Science Association Inc.

Chiba, "Poultry Nutrition and Feeding", Animal Nutrition Handbook, Section 12: Poultry Nutrition and Feeding, 2014, pp. 410-425, Lee I. Chiba.

Chojnacka et al., "The Possibilities of the Application of Algal Biomass in the Agriculture", Chemik, 2012, vol. 66, No. 111, pp. 1235-1248, Wrocław University of Technology, Wrocław, Poland.

"Curbing Antibiotic Use in Chickens", Feednavigator.com presentation, date unknown.

De Gussem, "Coccidiosis in Poultry: Review on Diagnosis, Control, Prevention and Interaction with Overall Gut Health", 16th European Symposium on Poultry Nutrition, 2007, pp. 253-261.

Ducatelle et al., "Biomarkers for Monitoring Intestinal Health in Poultry: Present Status and Future Perspectives", Veterinary Research, 2018, vol. 49, No. 43, 9 pages, BMC.

Durai et al., "Structure and Effects of Cyanobacterial Lipopolysaccharides", Marine Drugs, 2015, vol. 13, pp. 4217-4230.

Enzing et al., "Microalgae-Based Products for the Food and Feed Sector: An Outlook for Europe", JRC Scientific and Policy Reports, 2014, 82 pages, European Commission, Joint Research Center.

Fasina et al., "Characterization of Intestinal Immune Response to Clostridium Perfringens Infection in Broiler Chickens", Poultry Science, 2019, vol. 98, pp. 188-198, Oxford University Press.

Fernando et al., "Potential Anti-Inflammatory Natural Products from Marine Algae", Environmental Toxicology and Pharmacology, 2016, vol. 48, pp. 22-30, Elsevier B.V.

Filomena et al., "Marine Polysaccharides from Algae with Potential Biomedical Applications", Marine Drugs, 2015, vol. 13, pp. 2967-3028, MDPI.

Foi Summary, "Supplemental New Animal Drug Application", Dec. 12, 2007, 11 pages.

Ghiselli et al., "Isolation, Culture, and Characterization of Chicken Intestinal Epithelial Cells", BMC Molecular and Cell Biology, 2021, vol. 22, No. 12, 14 pages, BMC.

Guo et al., "Transcriptome Analysis in Chicken Cecal Epithelia Upon Infection by Eimeria Tenella In Vivo", PLOS One, May 2013, vol. 8, Issue 5, 10 pages.

Guo et al., "Inflammatory Responses to a Clostridium Perfringens Type A Strain and α-Toxin in Primary Intestinal Epithelial Cells of Chicken Embryos", Avian Pathology, 2015, vol. 44, No. 2, pp. 81-91, Taylor & Francis Group.

(56) References Cited

OTHER PUBLICATIONS

Guschina et al., "Lipids and Lipid Metabolism in Eukaryotic Algae", Progress in Lipid Research, 2006, vol. 45, pp. 160-186, Elsevier Ltd.

Habibi et al., "Anticoccidial Effects of Herbal Extracts on Eimeria Tenella Infection in Broiler Chickens: In Vitro and In Vivo Study", Journal of Parasitic Diseases, Apr.-Jun. 2016, vol. 40, No. 2, pp. 401-407, Springer.

Hammed et al., "Enzymatic Hydrolysis of Plants and Algae for Extraction of Bioactive Compounds", Food Reviews International, 2013, vol. 29, No. 4, pp. 352-370, Taylor & Francis Group.

Ibeagha-Awemu et al., "Bacterial Lipopolysaccharide Induces Increased Expression of Toll-Like Receptors (TLR) 4 and Downstream TLR Signaling Molecules in Bovine Mammary Epithelial Cells", Veterinary Research, 2008, vol. 39, No. 11, 12 pages, INRA, EDP Sciences.

Jurga et al., "Lipopolysaccharide From Rhodobacter Sphaeroides (TLR4 Antagonist) Attenuates Hypersensitivity and Modules Nociceptive Factors", Pharmaceutical Biology, 2018, vol. 56, No. 1, pp. 275-286, Taylor & Francis Group.

Keestra et al., "Chicken TLR21 is an Innate CpG DNA Receptor Distinct from Mammalian TLR9", The Journal of Immunology, 2010, vol. 185, pp. 460-467, American Association of Immunologists, Inc.

Kondo et al., "Primitive Extracellular Lipid Components on the Surface of the Charophytic Algal Klebsormidium Flaccidum and Their Possible Biosynthetic Pathways as Deduced from the Genome Sequence", Frontiers in Plant Science, Jun. 2016, vol. 7, Article 952, 15 pages.

Kraan, "Chapter 22, Algal Polysaccharides, Novel Applications and Outlook", 2012, pp. 489-532, http://dx.doi.org.10.5772/51572, Intech.

Kutuzova et al., "Diphosphoryl Lipid A From Rhodobacter Sphaergides Blocks the Binding and Internalization of Lipopolysaccharide in RAW 264.7 Cells", The Journal of Immunology, 2001, vol. 167, pp. 482-489, The American Association of Immunologists.

Leadbetter et al., "Metabolism of Acyl-Homoserine Lactone Quorum-Sensing Signals by Variovorax Paradoxus", Journal of Bacteriology, Dec. 2000, vol. 182, No. 24, pp. 6921-6926, American Society for Microbiology.

Lillehoj et al., "Quantitative Genetic and Functional Genomics Approaches to Investigating Parasite Disease Resistance and Protective Immune Mechanisms in Avian Coccidiosis", Animal Genomics for Animal Health, Developmental Biology (Basel), 2008, vol. 132, pp. 67-75, Basel, Karger.

Lu et al., "Anti-Inflammatory Effects of Non-Antibiotic Alternatives in Coccidia Challenged Broiler Chickens", The Journal of Poultry Science, 2014, vol. 51, pp. 14-21, Japan Poultry Science Association.

Macagno et al., "A Cyanobacterial LPS Antagonist Prevents Endotoxin Shock and Blocks Sustained TLR4 Stimulation Required for Cytokine Expression", Journal of Experimental Medicine (JEM), Jun. 12, 2006, vol. 203, No. 6, pp. 1481-1492, The Rockefeller University Press.

Mistry et al., "Inhibition of TLR2 Signaling by Small Molecule Inhibitors Targeting a Pocket Within the TLR2 TIR Domain", PNAS, Apr. 28, 2015, vol. 112, No. 17, pp. 5455-5460.

Muthamilselvan et al., "Herbal Remedies for Coccidiosis Control: A Review of Plants, Compounds, and Anticoccidial Actions", Evidence-Based Complementary and Alternative Medicine, 2016, vol. 2016, Article ID 2657981, 19 pages, Hindawi Publishing Corporation.

Nagao et al., "*Klebsormidium flaccidum*, a Charophycean Green Algal, Exhibits Cold Acclimation That is Closely Associated with Compatible Solute Accumulation and Ultrastructural Changes", Plant, Cell and Environment, 2008, vol. 31, pp. 872-885, Blackwell Publishing Ltd.

Nagao et al., "Sucrose Phosphate Phosphatase in the Green Alga *Klebsormidium flaccidum* (Streptophyta) Lacks an Extensive C-Terminal Domain and Differs from That of Land Plants", Planta, 2012, vol. 235, pp. 851-861, Springer-Verlag.

National Research Council, "Components of Poultry Diets", 1994, 16 pages, National Academies Press.

National Research Council, "Components of Feedstuffs Used in Poultry Diets", 1994, 19 pages, National Academies Press.

National Research Council, "Nutrient Requirements of Chickens", 1994, 16 pages, National Academies Press.

National Research Council, "Standard Reference Diets for Chicks", 1994, 3 pages, National Academies Press.

* cited by examiner

| | D14 | D28 | D42 |
|---|---|---|---|
| | | FCR | |
| 7. No Feed Additive | 1.518 | 1.683 | 1.708 |
| 8. Salinomycin | 1.577 | 1.638 | 1.673 |
| 9. Cocci Vaccine | 1.579 | 1.656 | 1.715 |
| 10. Zivo (1 lb/ton) - No Vaccine | 1.628 | 1.714 | 1.739 |
| 11. Zivo (0.5 lb/ton) - No Vaccine | 1.581 | 1.713 | 1.749 |
| 12. Zivo (0.5 lb/ton) - Vaccine | 1.527 | 1.622 | 1.684 |

| NQZ062019-45 Treatments | MEAN E. acervulina OPG | MEAN E. maxima OPG | MEAN E. tenella OPG | MEAN TOTAL OPGS |
|---|---|---|---|---|
| 1. No Feed Additive - Cocci Challenge | 94036 | 2257 | 834 | 97126 |
| 2. Vaccine Control | 44300 | 2990 | 6092 | 53382 |
| 3. No Feed Additive - No Cocci Challenge | 17020 | 1545 | 600 | 19165 |
| 4. Vaccine + Zivo (1/2/0.5 pound/ton) | 2913 | 1701 | 2134 | 6748 |
| 5. Vaccine + Zivo (1/1/0.5 pound/ton) | 5425 | 1957 | 3202 | 10583 |
| 6. Vaccine + Zivo (0/1.5/0 pound/ton) | 1690 | 1312 | 6381 | 9382 |
| 7. Vaccine + Zivo (1/1/0 pound/ton) | 4513 | 6270 | 26847 | 37630 |

ENHANCEMENT OF VACCINE EFFICACY VIA BIOMASS AND/OR RELATED MATERIAL IN ANIMAL DRINK AND FEED

CROSS REFERENCE TO RELATED APPLICATION

This application is a US. Non-provisional Patent Application of U.S. Provisional Patent Application No. 63/047, 517, entitled "Enhancement of Vaccine Efficacy Via Biomass and/or Related Material In Animal Feed," filed Jul. 2, 2020, which is herein incorporated by reference in its entirety for all purposes.

TECHNICAL FIELD

The present invention relates to the use of a bacteria-based compound in conjunction with an appropriate vaccine in the prevention and treatment of disease. More particularly, the present invention relates to the use of a compound such as that derived from a substance produced by gram negative bacteria such as, but not limited to, a lipopolysaccharide (LPS) of gram negative bacteria in conjunction with an appropriate vaccine in the prevention and treatment of an intestinal tract disease such as coccidiosis by way of an animal feed regimen administered from the day of hatch onward.

BACKGROUND OF THE INVENTION

Substantial economic losses in the poultry industry are most often the result of disease. Diseases in flocks often result in reduced production volume or compromised quality of meat. Prevention and treatment of poultry disease adds significantly to poultry production costs. Some estimates place total losses as a result of poultry disease at more than 10% of all production costs.

Of the diseases known to strike poultry flocks, the most common are enteric diseases, which include coccidiosis, a disease caused by a parasite, the coccidian protozoa. Annual economic losses due to coccidiosis alone are estimated to exceed $3 billion per year and these costs are expected to increase due to a variety of reasons.

First, coccidiosis prevention today is accomplished mainly through the use of vaccines. A one-time administration of the vaccine is given very early in broiler life and, specifically, on the day of hatch. While this approach has shown some benefit, vaccines are known to suffer from variable effectiveness in controlling the disease over time. Experimentation has shown that a vaccine used in conjunction with a supplement such as a probiotic may improve outcome, but this approach adds to production cost.

Second, coccidiosis treatment today is accomplished conventionally through the use of antibiotics and ionophores, both of which are added costs in an industry with constricting margins. The use of antibiotics and ionophores is under pressure globally for a number of reasons, including environmental. Relatively recently, the European Union banned sub-therapeutic doses of certain antibiotics for use as feed additives. Synthetic treatment compounds and other chemical agents are known but are not as effective as conventional antibiotics.

Third, the above-noted pressure against using antibiotics and ionophores notwithstanding, one or both antibiotics and ionophores are often used in a series with a staggered approach (bioshuttling) in which live coccidiosis vaccine is administered at the hatchery followed by treatment with an anti-coccidial between two and three weeks of age.

Fourth, drug resistance to antibiotics, ionophores, and synthetic treatment compounds is increasing largely due to overuse thereby severely compromising the effectiveness of these treatments. There has been no approval of new drugs in any of these categories for many years.

Fifth, even if known treatments were still economical and effective, known approaches would still be regarded as unsatisfactory because the medication must be included in the animal's feed for the full duration of its lifespan to be fully effective. This requirement adds significant cost to feed for the entire growout period.

Accordingly, it is desirable to develop a treatment method that boosts the effectiveness of vaccines for use in the treatment of pathogenic infections such as, but not limited to, coccidiosis in animals without neutralizing the activity of the vaccine itself.

SUMMARY OF THE INVENTION

The disclosed inventive concept provides an improved treatment method for a broad variety of diseases in both animals and humans. The method includes combining one or more vaccines with a treatment compound set forth as part of the disclosed inventive concept that enhances vaccine efficacy. Unlike the unworkable combination of an anti-coccidia agent with a vaccine, the treatment compound may be combined with a vaccine because the treatment compound does not act on the pathogens directly. An added advantage of the disclosed inventive treatment method over known treatment methods is concomitant use with a vaccine without the risk of treatment resistance.

The vaccines used to control coccidiosis in poultry have historically been of the live coccidian vaccine variety. Known vaccines contain sporulated oocysts of various species. It is known that the parasites *E. maxima*, *E. tenella*, and *E. acervulina* generally exist in vaccines. The total number of oocysts present in each of today's vaccines differs significantly. The total number may be as low as about 200 oocysts per dose to as high as about 3000 oocysts per dose.

A number of methods are known for delivering live oocyst vaccines. These methods include delivery through drinking water, administration through feed by either spraying the feed or applying gel droplets to the feed, or administration at the hatchery through gel bead delivery, ocular vaccination, or spray cabinets, the latter being the most common method of administration in the United States today. When using the spray cabinet for coccidian vaccination, the chicks are a day old at the time of treatment.

When a compound, such as, but not limited to, the disclosed compound is used in conjunction with one or more vaccines, a synergistic effect is realized. The suggested compound is derived from a substance produced by gram negative bacteria such as, but not limited to, a lipopolysaccharide (LPS) of gram negative bacteria. The treatment compound is combined with one or more appropriate vaccines and is administered early in the life of an animal, providing a synergistic effect compared to the use of the treatment compound or the vaccine alone.

DESCRIPTION OF THE DRAWINGS

For a more complete understanding of this invention, reference should now be made to the accompanying figures. As set forth in many of the figures, the designation "No Tx, No Challenge" refers to a test in which no treatment was administered to a subject animal not deliberately infected with coccidiosis. The designation "No Tx, Cocci" refers to a test in which no treatment was administered to a subject animal deliberately infected with coccidiosis. The designation "Anti-cocci, Cocci" refers to a test in which the subject animal was infected with coccidiosis and the animal was administered an anticoccidial.

The designation "ZIVO all rations, Cocci" refers to a test in which the subject animal was infected with coccidiosis and the animal was administered a treatment composition according to the disclosed inventive concept. The designation "ZIVO starter & grower, Cocci" refers to a test in which the subject animal was infected with coccidiosis and the animal was administered a starter diet at 0-21 day of age. The designation "ZIVO starter, Cocci" refers to a test in which the subject animal was infected with coccidiosis and the animal was administered a grower diet at 22-35 days of age. The designation "ZIVO, grower & finisher, Cocci" refers to a test in which the subject animal was infected with coccidiosis and the animal was administered a grower and finisher diet at 36-42 days of age.

The accompanying figures are described as follows:

FIG. 1 is a graph illustrating test subject feed conversion corrected data for Days 0 to 42 from the First Study;

FIG. 2 is a graph illustrating test subject feed conversion corrected data for Days 0 to 41 from the First Study;

FIG. 3 is a graph illustrating non-adjusted feed conversion ratio by treatment over the first study from the First Study;

FIG. 4 is a graph illustrating test subject percent mortality days 0 to 42 from the First Study;

FIG. 5 is a graph illustrating test subject percent mortality days 0 to 41 from the First Study;

FIG. 6 is a graph illustrating test subject average lesion score day 26 from the First Study;

FIG. 7 is a graph illustrating test subject average lesion score for day 27 from the First Study;

FIG. 8 is a graph illustrating mean *Eimeria* sp lesion scores by species from the First Study;

FIG. 9 is a graph illustrating mean oocysts per gram (OPG) by coccidia species from the First Study;

FIG. 10 is a graph illustrating mean *Eimeria* sp lesion scores by species from the First Study; and FIG. 11 is a graph illustrating mean oocysts per gram (OPG) by coccidia species from the First Study.

DETAILED DESCRIPTION OF THE PREFERRED EMBODIMENT

Figure 1:
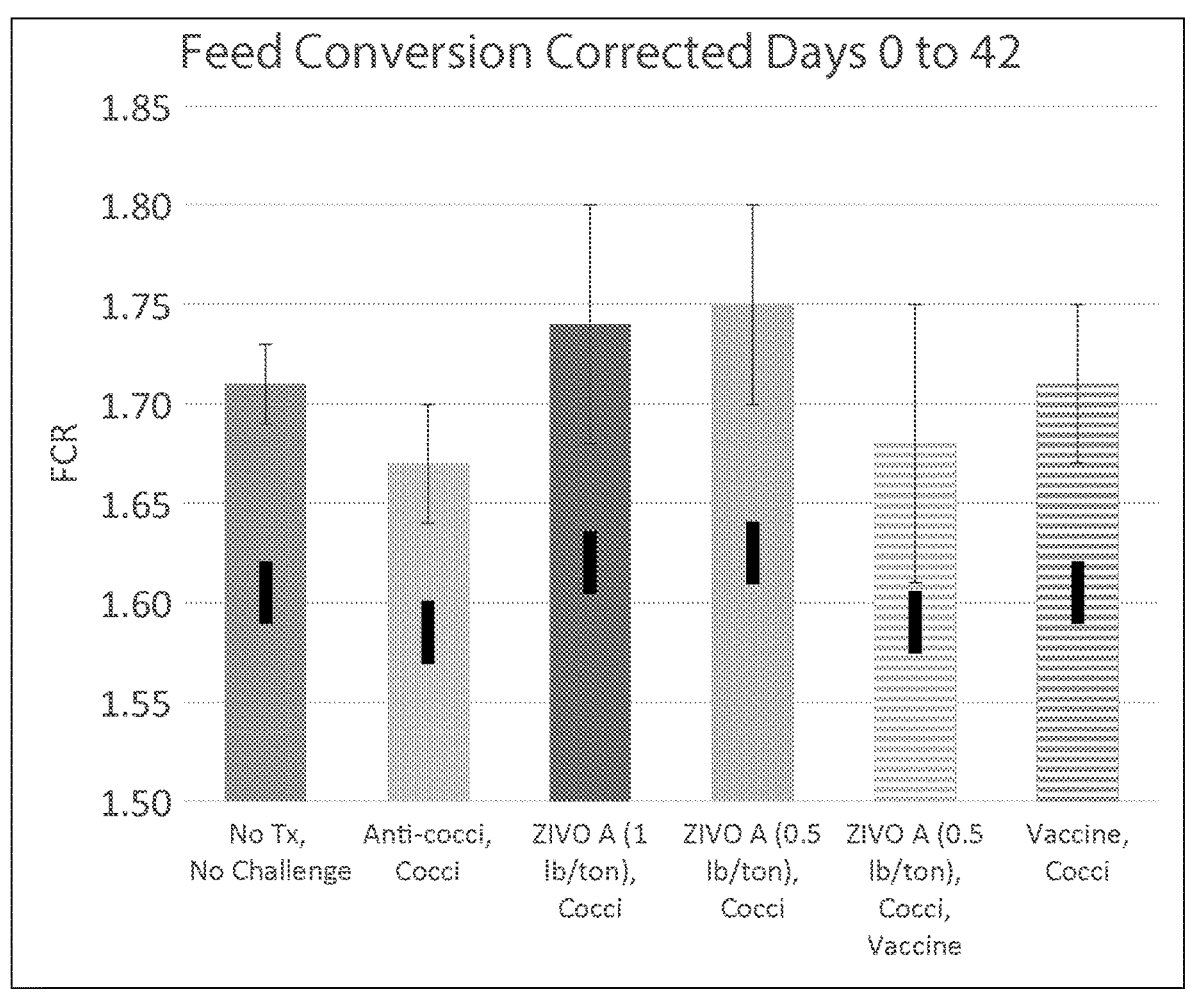

In the following description, various operating parameters and components are described for different constructed embodiments. These specific parameters and components are included as examples and are not meant to be limiting. Unless otherwise noted, all technical and scientific terms used herein are to be accorded their common meanings as would be understood by one having ordinary skill in the art.

The Compound Used in Treatment

The disclosed method of treatment preferably, but not absolutely, utilizes a compound generally derived from a gram negative bacteria such as, but not limited to, a lipopolysaccharide (LPS) of gram negative bacteria. By administering the compound early in broiler life, disease prevention and treatment via immune modulation are achieved.

As used herein, the term "algal culture" is defined as an algal organism and bacteria (one or more types) that grow together in a liquid medium. Unless expressly stated otherwise, the term "algal biomass" refers to the algal cells and bacterial cells (with the liquid culture medium removed). The "algal biomass" can be wet material or dried material.

Unless expressly stated otherwise, the term "algal supernatant" is defined as the culture medium in which the algal biomass is grown that contains excreted compounds from the algal biomass. Algal supernatant is obtained by growing algal biomass in culture medium for an appropriate length of time and then removing the algal and bacterial cells by filtration and/or centrifugation.

It is known that bacteria of the Variovorax genus and the *Rhodobacter* genus are metabolically versatile. Variovorax is a gram negative aerobic bacterium that can grow under a variety of conditions. It is part of the subclass Proteobacteria and is capable of metabolically utilizing several natural compounds generated by plants or algae. *Rhodobacter* can grow under a broad variety of conditions, including both photosynthesis and chemosynthesis. Growth can also be achieved under both anaerobic and aerobic conditions. *Rhodobacter sphaeroides* represents a gram negative facultative bacterium and is a member of the α-3 subdivision of the Proteobacteria.

Embodiments of the compound used in the treatment of disease as set forth herein include one or more LPS/Lipid A compounds produced by gram negative bacterial strains for use as selective modulators of the TLR4 signaling pathway.

The disclosed inventive concept involves any combination of three fundamental steps: (1) the gram negative bacteria produces LPS/Lipid A compounds; (2) the LPS/Lipid compounds modulate TLR4 activity; and (3) a downstream effect results in enhancement of innate and adaptive immune processes, thereby aiding in the treatment of coccidiosis.

In an embodiment, the LPS/Lipid A compounds used as selective modulators of the TLR4 signaling pathway are produced from a *Variovorax paradoxus* strain. The *Variovorax paradoxus* strain may be a naturally occurring strain found in an algal biomass and/or algal supernatant products. For example, the algal biomass may comprise the algal species *Klebsormidium flaccidum*. More specifically, the algal biomass culture may comprise the algal strain *Klebsormidium flaccidum*, var. ZIVO.

In another embodiment, the LPS/Lipid A compounds used as selective modulators of the TLR4 signaling pathway are produced from a *Rhodobacter sphaeroides* strain. Extensive studies have been undertaken regarding the structure and function of *Rhodobacter sphaeroides*. More focused studies have examined the photosynthetic characteristics of *Rhodobacter sphaeroides*. While it is known that lipopolysaccharides from *Rhodobacter sphaeroides* are effective TLR4 antagonists in human cells that prevent TLR4-mediated inflammation by blocking LPS/TLR4 signaling, the inventors employed a testing methodology to address multiple immune response mechanisms in poultry to arrive at the conclusion that an LPS compound derived from *Rhodobacter sphaeroides* proved effective as a treatment of coccidiosis in poultry. Research demonstrated that combining a TLR4 modulator with an activator of TLR2 (such as LPS from gram negative bacteria) appears to provide an anti-coccidiosis effect.

Accordingly, embodiments of the compound used in the treatment of disease according to the present disclosure are directed to one or more LPS/Lipid A compounds produced by a gram negative bacterial strain of the group Variovorax or the group *Rhodobacter* for use as selective modulators of the TLR4 signaling pathway. A specific embodiment of the disclosed inventive concept is directed to the use of an LPS/Lipid A compound used as a selective modulator of the TLR4 signaling pathway produced from the *Variovorax paradoxus* strain and the *Rhodobacter sphaeroides* strain.

The LPS/Lipid A compound employed herein may be obtained from the *Variovorax paradoxus* strain and/or the *Rhodobacter sphaeroides* strain by any suitable method, but in specific embodiments they are extracted using standard multi-step LPS extraction protocols, such as: (1) extracting freeze-dried bacteria with a solution of phenol/guanidine thiocyanate and collecting the water layer for freeze-drying; (2) resolubilizing the freeze-dried fraction in water; (3) ultrafiltration of the solubilized fraction to remove low molecular weight substances and salts; (4) affinity purifying the high-molecular weight fraction using a polymyxin B resin column such as Affi-prep polymyxin matrix material (Bio-Rad), from which an active fraction is eluted with 1% deoxycholate and, optionally; (5) performing additional purification using size-exclusion chromatography.

In some examples, multiple types of LPS extraction protocols are employed to obtain an LPS compound from the bacteria, and extraction procedures may be performed more than once. Once the LPS compound is extracted and purified from the bacteria, the Lipid A fraction may be prepared by acid hydrolysis or other suitable technique.

The one or more LPS/Lipid A compounds derived from gram negative bacterial strains, such as *Variovorax paradoxus* or *Rhodobacter sphaeroides*, may selectively modulate the TLR4 signaling pathway to alter inflammatory responses and to improve immune health in a variety of uses and applications. In an embodiment, the LPS/Lipid A compound derived from *Variovorax paradoxus* or *Rhodobacter sphaeroides* may be incorporated within an algal-based feed ingredient to improve gut health of poultry.

The disclosed LPS/Lipid A compound derived from *Variovorax paradoxus* or *Rhodobacter sphaeroides* may be used to improve the health of poultry through a variety of mechanisms.

Specific Treatment Compounds

The disclosed treatment compounds are based on one or more fresh water algal biomasses including bacterial strains as discussed above. More particularly, the algal biomass may include the Gram negative such as *Variovorax paradoxus* strain or Gram negative *Rhodobacter sphaeroides* strain.

The compounds share the common characteristic of the algal biomass referenced above and are used in animal treatment. The algal biomass-based products are fed to animals in a formulated diet such as a corn or corn-soybean meal (SBM) diet or are delivered in drinking water.

In all of is variations the ZIVO treatment compound is fresh water biomass containing gram negative bacteria and any products derived therefrom provided as animal drink and/or feed in combination of a feed additive, such as soy oil, preferably though not exclusively at a ratio of two parts soil oil to one part algal biomass. Once the biomass and feed additive are combined to the preferred premix level, the combined batch is poured or administered evenly into a ribbon mixer containing finished feed. The biomass is preferably provided in an amount of between about 0.1 lbs. composition per ton of finished feed to about 10.0 lbs. composition per ton of finished feed, is more preferably provided in an amount of between about 0.2 lbs. composition per ton of finished feed to about 5.0 lbs. composition per ton of finished feed, and is most preferably provided in an amount of between about 0.5 lbs. composition per ton of finished feed to about 2.0 lbs. composition per ton of finished feed. The ideal suggested and non-limiting ratio is about 0.5, 1.0, and 2.0 composition per ton of finished feed when used in conjunction with a vaccine.

Treatment Method

A non-limiting example of a method for the enhancement of a vaccine in poultry is set forth. It is to be understood that the following method is not intended as being the sole treatment method but is only exemplary. The studies set forth herein compare the disclosed inventive compound to the ionophorous anticoccidial drug, Salinomycin, and with day old coccidia vaccination. Treatment was provided to separate groups. However, no single group was treated with both an anticoccidial drug and a vaccine. All birds except a negative control group were challenged with *Eimeria acervulina, E. maxima*, and *E. tenella* on day 21.

Testing in all three studies set forth below was undertaken using a high oocyst dose vaccine, Coccivac-B52 (trademark, Intervet Inc.), a product sold by Merck Animal Health. According to the manufacturer, Coccivac-B52 contains *E. acervulina, E. maxima, E. mivati*, and *E. tenella*. The vaccine was mixed with water at a dosage of 240 ml of water per 1,000 doses. The vaccine-water combination was placed in a sealed vaccine container and mixed by stirring and inversion of the container. The mixed vaccine-water combination was sprayed onto each chick when one day old in a conventional spray cabinet. It was estimated that each chick ingested an equal number of droplets so as to result in the ingestion of about 240 µL dose per chick.

The live coccidia vaccination (Coccivac-B52 [Merck]) was administered to day old chicks in the studies according to the manufacturer's recommendation and the test groupings described in the tables to follow below.

First Study

The objective of the first study was to determine the most effective dose regime for the disclosed inventive natural product.

The rations consisted of non-medicated commercial-type broiler starter, grower, and finisher diets compounded according to NRC guidelines and contained feedstuffs commonly used in the United States. As a common regime rations for some but not necessarily all studies were fed ad libitum from date of chick arrival as follows: Starter—DOT 0 until DOT 14, grower DOT 14 to DOT 28, and finisher from DOT 28 to DOT 42 (study termination).

Diets were fed as crumbles in starter and pellets in grower and finisher. Experimental treatment feeds were prepared from a basal feed formulation. Quantities of all basal feed and test articles included in treatment group batches were documented and included with source data files. Treatment feeds were mixed prior to pelleting to assure uniform distribution of respective test articles.

TABLE 1

| | | | | | DOSAGE | | |
|---|---|---|---|---|---|---|---|
| TREATMENT GROUP | TREATMENT | # OF REPLICATES | COCCI VACCINE | COCCI CHALLENGE | STARTER DOT 0-14 | GROWER DOT 14-35 | FINISHER DOT 35-42 |
| 7 | No Feed Additive | 10 | No | Yes | | | |
| 8 | Salinomycin | 10 | No | Yes | 60 gms/ton | 60 gms/ton | 60 gms/ton |
| 9 | Vaccine | 10 | Yes | Yes | | | |
| 10 | Zivo | 10 | No | Yes | 1 lb/ton | 1 lb/ton | 1 lb/ton |
| 11 | Zivo | 10 | No | Yes | 0.5 lb/ton | 0.5 lb/ton | 0.5 lb/ton |
| 12 | Zivo | 10 | Yes | Yes | 0.5 lb/ton | 1.0 lb/ton | 1.0 lb/ton |

Fifteen hundred birds (1,500) were assigned to six (6) treatment groups with ten (10) replicate pens per treatment and 25 birds per pen. The study began when birds were placed (day-of-hatch; DOT 0), at which time birds were allocated to experimental pens. Only healthy birds were selected. On DOT 0, group body weights were recorded by pen. No birds were replaced during the course of the study. Analysis Methodology-First Study Birds received treatment-appropriate feed from day 0 to day 42. On day 14, remaining starter feed was removed, weighed, and replaced with grower feed to day 28. On day 28, the remaining grower feed was removed, weighed back, and replaced with finisher feed to day 42.

On Day 20 of the study all birds received a mixed *E. acervulina, E. maxima*, and *E. tenella* coccidial inoculum (100,000 oocysts per bird of *E. acervulina;* 50,000 oocysts per bird of *E. maxima;* and 75,000 oocysts per bird of *E. tenella*). The inoculum was mixed into the feed found in the base of each pen's tube feeder.

On Day 26, three birds from each pen were selected, sacrificed, weighed, and examined for the degree of presence of coccidia lesions. The Johnson and Reid (1970) method of coccidiosis lesion scoring was used to score the infected region(s) of the intestine. The scoring was based on a 0 to 4 score, with 0 being normal and 4 being the most severe.

On Day 26, fresh fecal samples were collected from each pen. These representative samples were tested to determine the degree of oocysts shedding/cycling. Oocysts per gram feces were determined for each sample.

On Day 42, the trial was terminated.

TABLE 1

Day 0 to 14 Performance Results

| Treatment | Feed Intake | Adjusted FCR* | Non-Adjusted FCR | Weight Gain (kg) |
|---|---|---|---|---|
| 1. No Feed Additive | 11.62A | 1.52A | 1.53A | 0.31AB |
| 2. Salinomycin | 11.48A | 1.58A | 1.60A | 0.31B |
| 3. Cocci Vaccine | 11.62A | 1.58A | 1.59A | 0.30B |
| 4. Zivo (1 lb/ton) - No Vaccine | 12.09A | 1.63A | 1.65A | 0.31AB |
| 5. Zivo (0.5 lb/ton) - No Vaccine | 12.45A | 1.58A | 1.59A | 0.33A |
| 6. Zivo (0.5 lb/ton) - Vaccine | 12.31A | 1.53A | 1.54A | 0.33A |

*Feed conversion ratio adjusted for mortality

TABLE 2

Day 0 to 28 Performance Results

| Treatment | Feed Intake | Adjusted FCR* | Non-Adjusted FCR | Weight Gain (kg) |
|---|---|---|---|---|
| 1. No Feed Additive | 39.74BC | 1.68AB | 1.86A | 1.00B |
| 2. Salinomycin | 38.69C | 1.64B | 1.78AB | 1.01B |
| 3. Cocci Vaccine | 41.19AB | 1.66AB | 1.72BC | 1.03B |
| 4. Zivo (1 lb/ton) - No Vaccine | 40.27BC | 1.71A | 1.78AB | 1.01B |
| 5. Zivo (0.5 lb/ton) - No Vaccine | 40.86B | 1.71A | 1.82AB | 1.02B |
| 6. Zivo (0.5 lb/ton) - Vaccine | 43.05A | 1.62B | 1.65C | 1.11A |

*Feed conversion ratio adjusted for mortality

TABLE 3

Day 0 to 42 Performance Results

| Treatment | Feed Intake | Adjusted FCR* | Non-Adjusted FCR | Weight Gain (kg) | Percent Mortality | Cocci Percent Mortality |
|---|---|---|---|---|---|---|
| 1. No Feed Additive | 82.46B | 1.71AB | 1.84A | 2.41AB | 17.20A | 9.60A |
| 2. Salinomycin | 80.16B | 1.67B | 1.81AB | 2.39AB | 18.00A | 8.40A |
| 3. Cocci Vaccine | 85.12AB | 1.71AB | 1.82AB | 2.37AB | 13.60AB | 3.20B |
| 4. Zivo (1 lb/ton) - No Vaccine | 85.00AB | 1.74A | 1.83A | 2.36B | 13.60AB | 2.80B |
| 5. Zivo (0.5 lb/ton) - No Vaccine | 84.88AB | 1.75A | 1.86A | 2.37AB | 14.80AB | 5.60AB |
| 6. Zivo (0.5 lb/ton) - Vaccine | 90.07A | 1.68B | 1.75B | 2.48A | 9.20B | 2.40B |

*Feed conversion ratio adjusted for mortality

Figure 2:
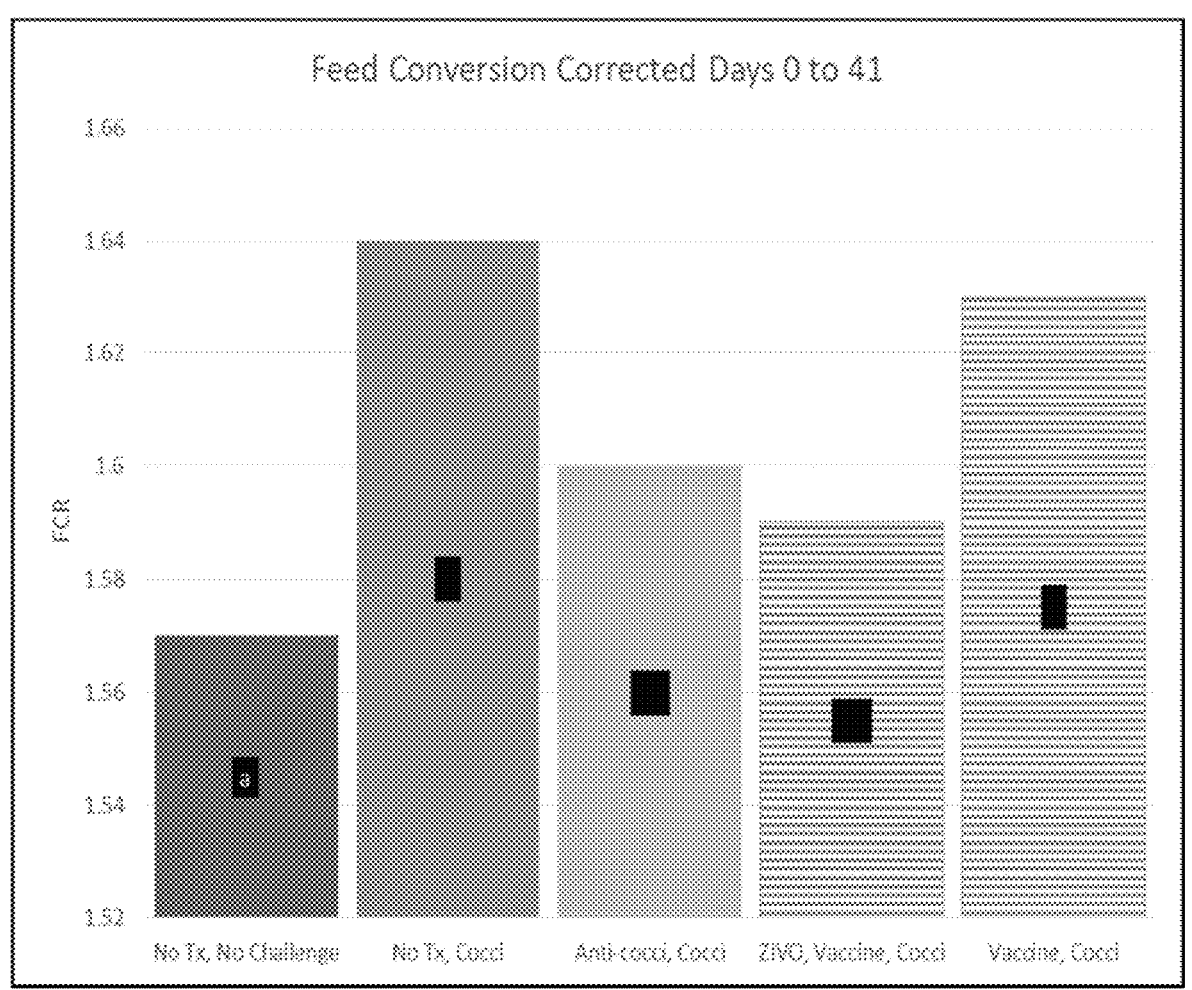

The Feed Corrected Days 0 to 42 illustrated in FIG. 1 and the Feed Corrected Days 0 to 41 illustrated in FIG. 2 are taken from exemplary studies and are not intended as being limiting. Instead, the data represented therein provides general background information.

TABLE 4

| Mean Coccidia Lesion Scores* | | | | |
| --- | --- | --- | --- | --- |
| Treatment* | *E. acervulina* | *E. maxima* | *E. tenella* | Average |
| 1. No Feed Additive | 2.23A | 1.87A | 2.30AB | 2.13AB |
| 2. Salinomycin | 1.80BC | 1.93A | 2.17AB | 1.97BC |
| 3. Cocci Vaccine | 1.67C | 1.90A | 2.03B | 1.87BC |
| 4. Zivo (1 lb/ton) - No Vaccine | 2.07AB | 1.83A | 2.30AB | 2.07ABC |
| 5. Zivo (0.5 lb/ton) - No Vaccine | 2.27A | 2.03A | 2.60A | 2.30A |
| 6. Zivo (0.5 lb/ton) - Vaccine | 1.63C | 1.70A | 2.07B | 1.80C |

*Johnson and Reed on DOT 26

TABLE 5

| Results of Oocysts per gram (OPG) of Feces* | | | | |
| --- | --- | --- | --- | --- |
| Treatment | OPG A | OPG M | OPG T | Total OPG |
| 1. No Feed Additive | 36171AB | 2214A | 794A | 39180AB |
| 2. Salinomycin | 49418AB | 2615A | 834A | 52866AB |
| 3. Cocci Vaccine | 22498B | 1287A | 467A | 24252B |
| 4. Zivo (1 lb/ton) - No Vaccine | 81227A | 2788A | 2288A | 86303A |
| 5. Zivo (0.5 lb/ton) - No Vaccine | 51346AB | 12500A | 193A | 64039AB |
| 6. Zivo (0.5 lb/ton) - Vaccine | 36905AB | 2781A | 1628A | 41314AB |

*OPG from feces on DOT 26

Results-First Study

Figure 3:
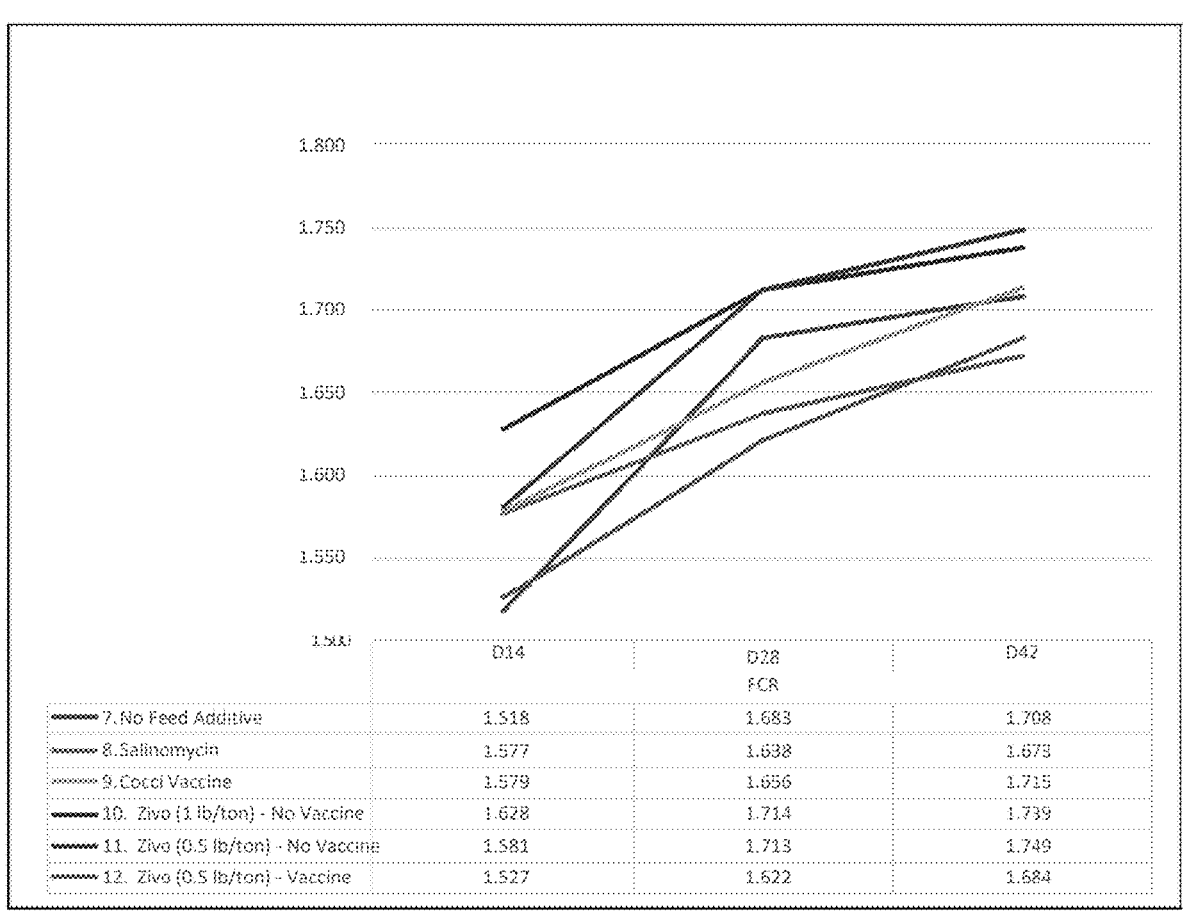

The peak of coccidia vaccine reaction for treatments 3 and 6 was about 14 days. The vaccine with the inventive composition in the starter had significantly heavier body weight and numerically lower FCR than the vaccine only treatment at 14 days (Table 1). The coccidia challenge occurred on day 20 with peak damage day 25 to 27. The vaccine and inventive composition continued to have statistically heaviest body weight and lowest FCR (Table 2). The one pound/ton of inventive composition continuously had similar performance to the drug, Salinomycin. The 42 day results demonstrated the combination of vaccine with the inventive composition had body weights numerically heavier than the challenged control birds and 11 points heavier than the vaccine alone (Table 3). The vaccine with the inventive composition had significantly lower non-adjusted FCR to the no treatment (FIG. 3).

Figure 4:
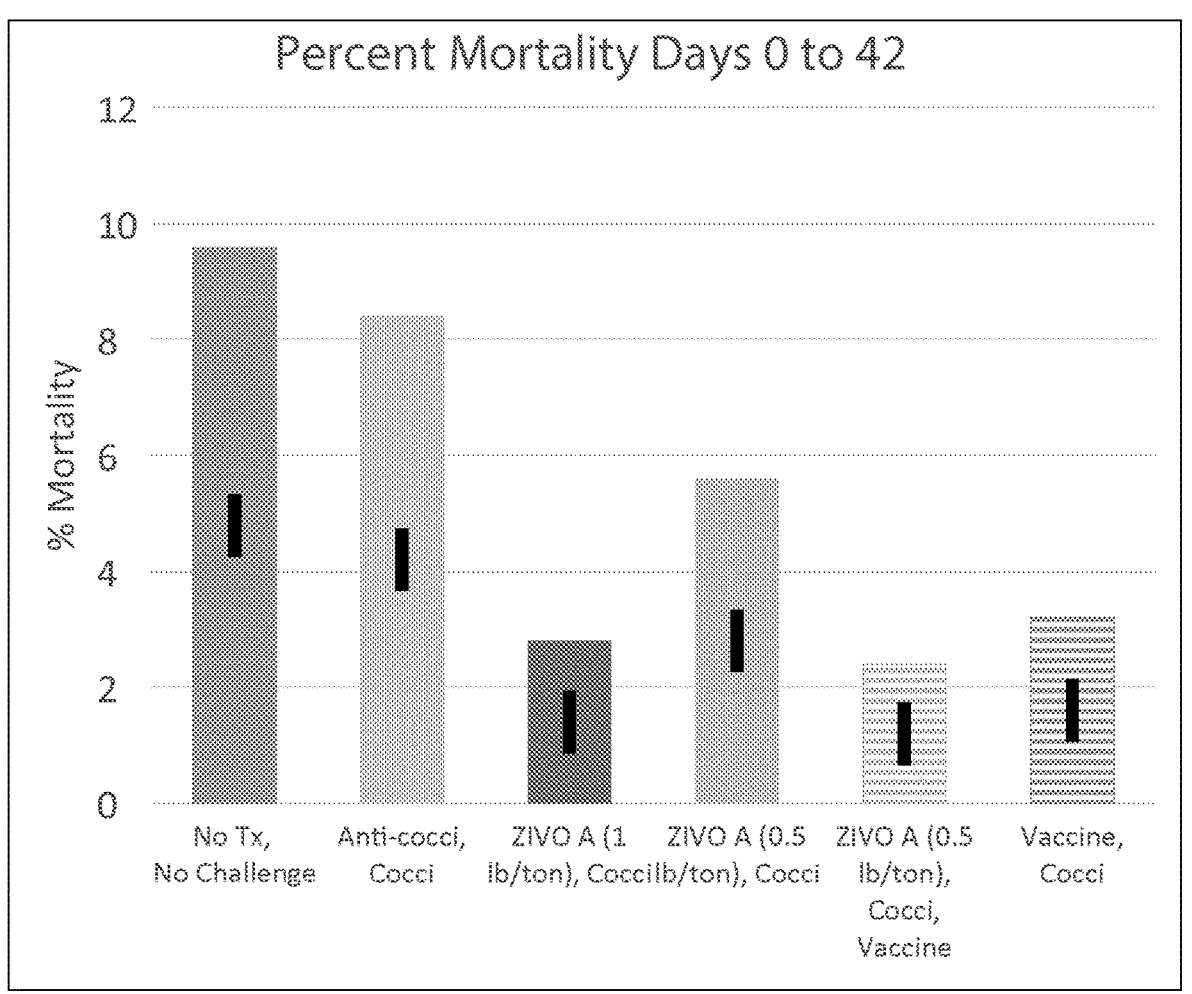
Figure 5:
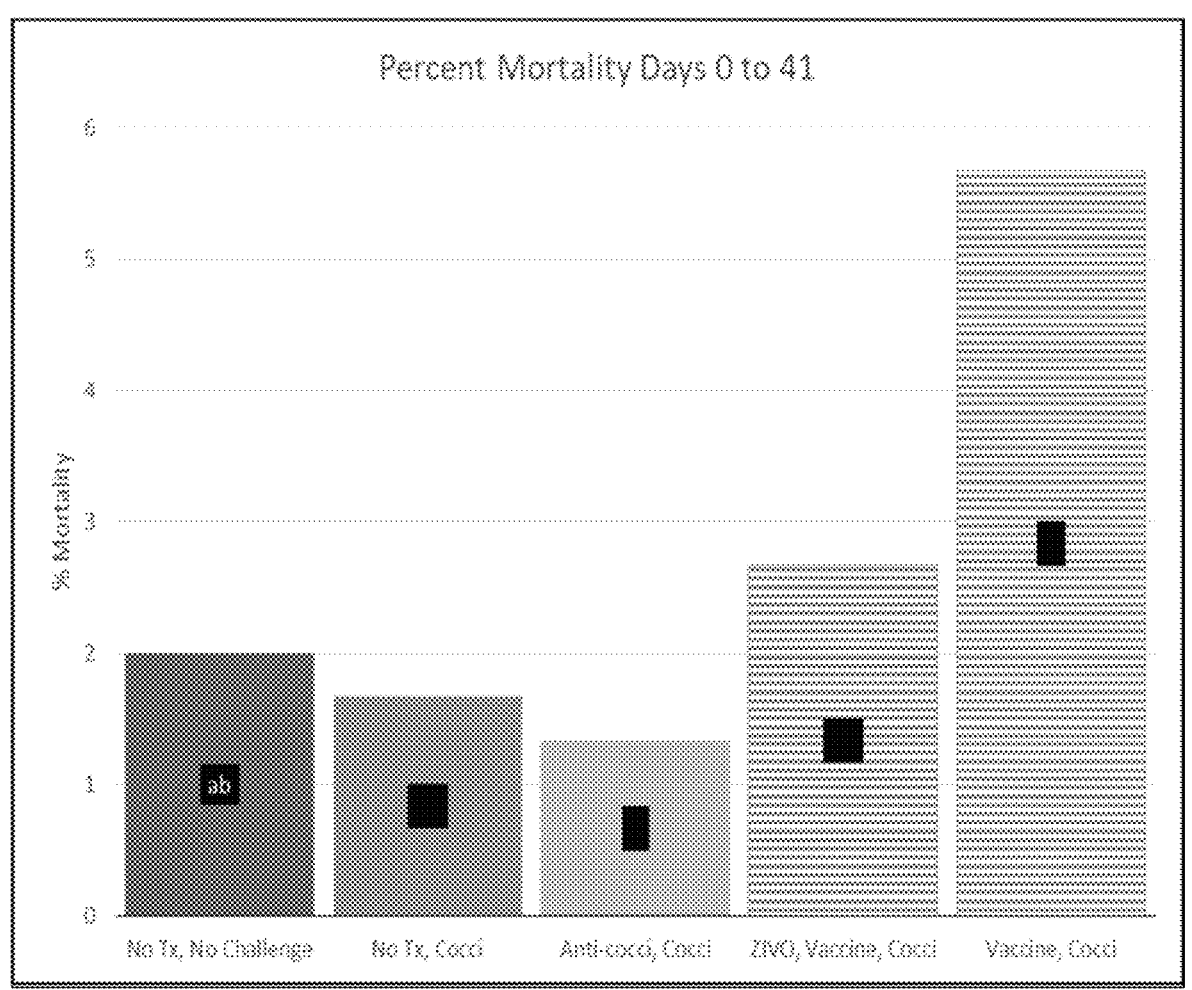
Figure 6:
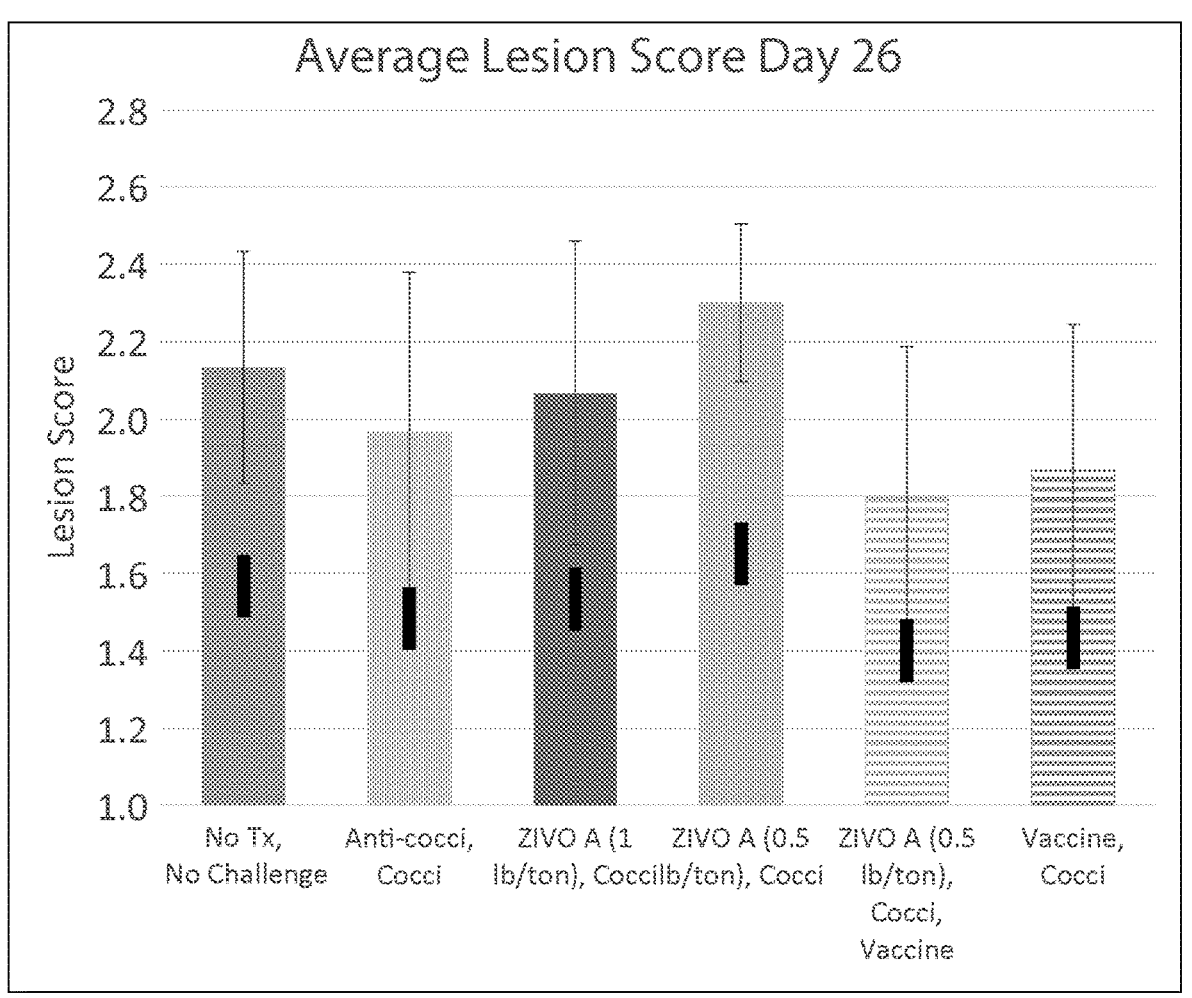
Figure 7:
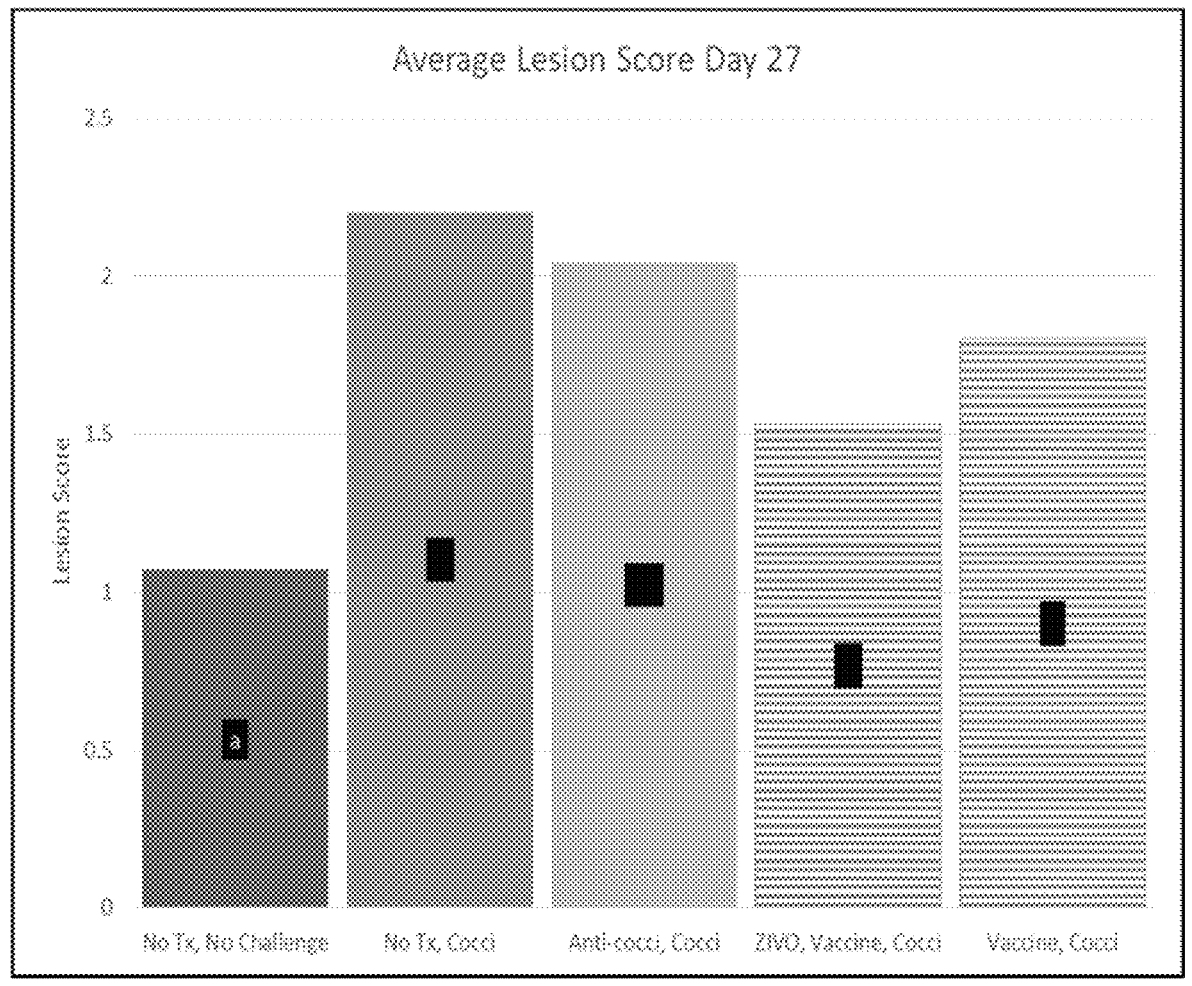
Figure 8:
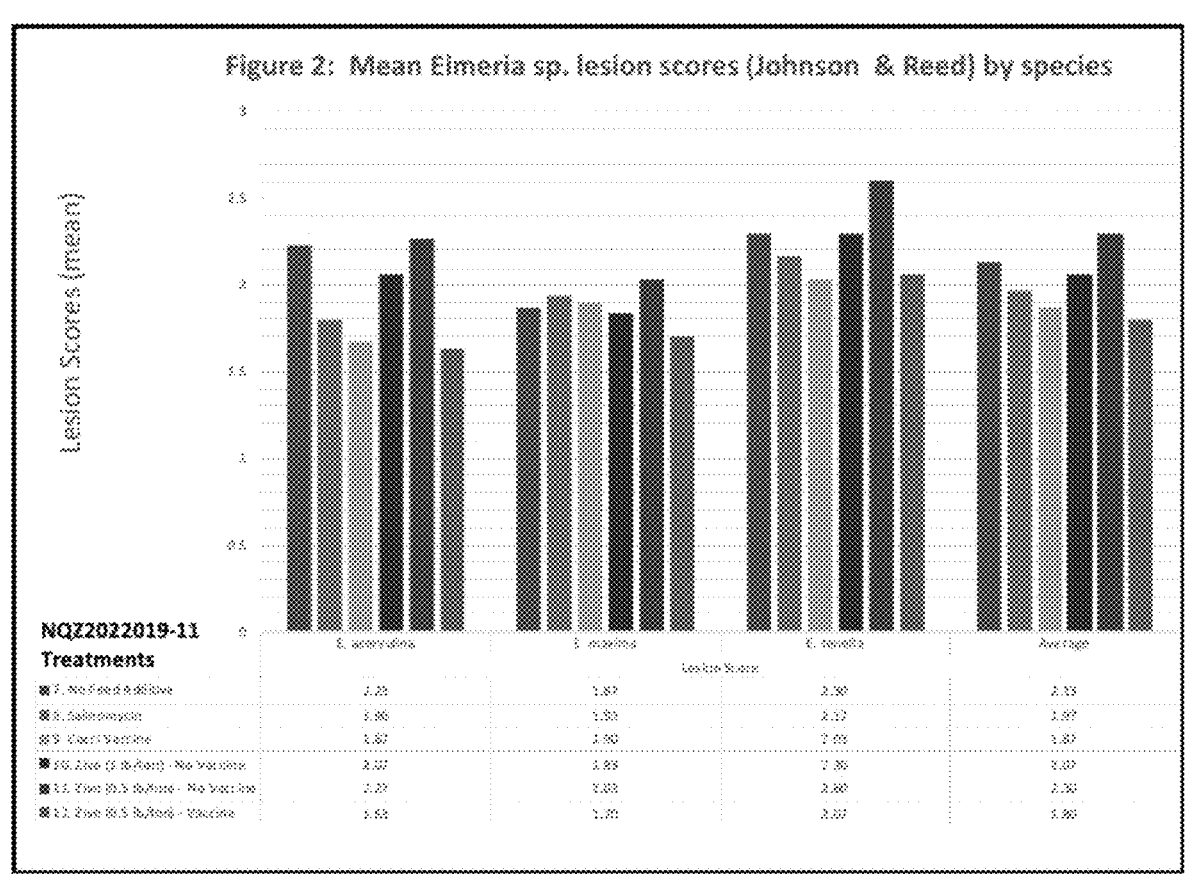
Figure 9:
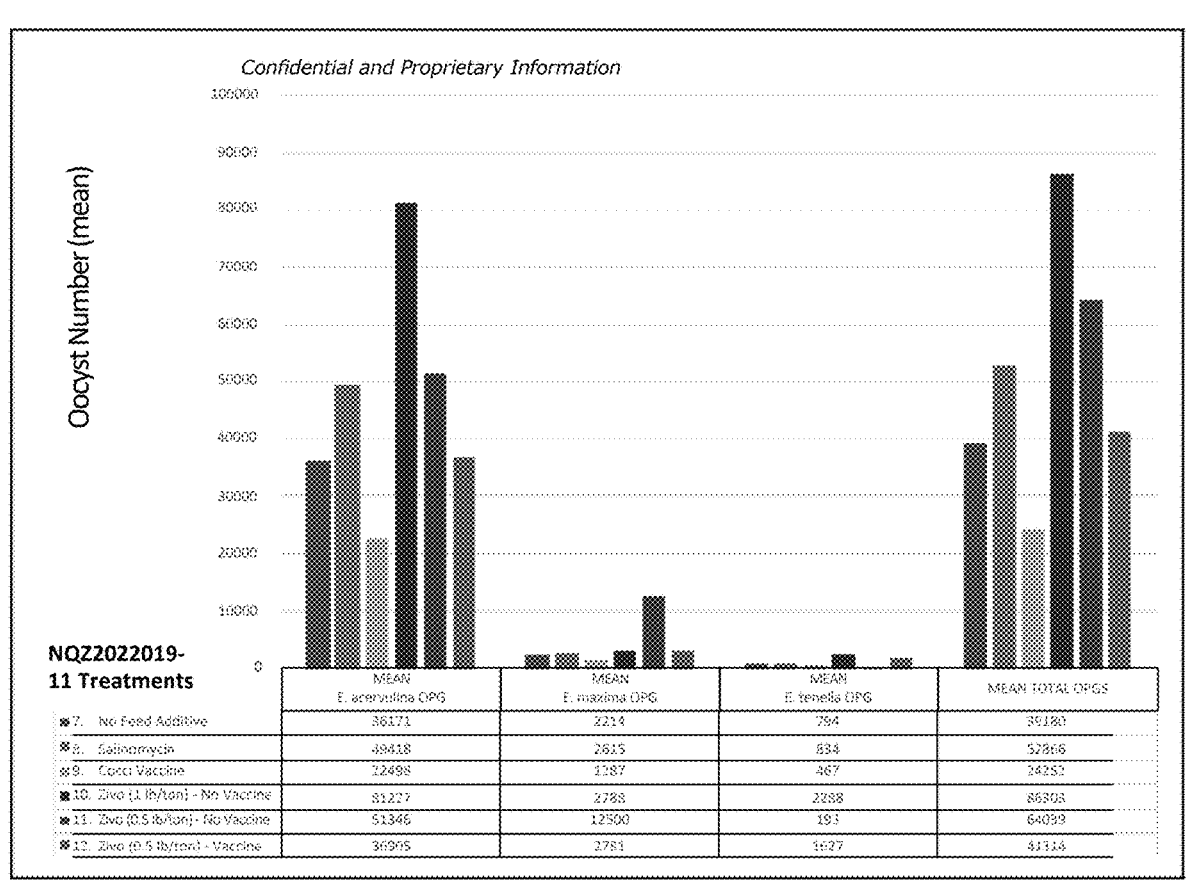

As illustrated in FIG. 4 ("Percent Mortality Days 0 to 42" and FIG. 5 ("Percent Mortality Days 0 to 41") there was higher mortality after the challenge attributed to the coccidia. Interestingly, the vaccine alone and all inventive composition treatments were significantly less than the challenge control and even the Salinomycin (Table 3). The mean Johnson and Reed lesion scores for all cocci were significantly lower in the vaccine with Zivo (Table 4, FIG. 6 ["Average Lesion Score Day 26"], and FIG. 7 ["Average Lesion Score Day 27"]). This was especially true for *E. acervulina* and *E. maxima* (FIG. 8). This most likely explains better performance in this treatment. The OPG results follow a similar trend (Table 5). However, OPGs do not correlate to treatment performance as well as the lesion scores (FIG. 9).

Second Study

Rations consisted of non-medicated commercial-type broiler starter, grower, and finisher diets compounded according to NRC guidelines and contain feedstuffs commonly used in the United States. Day-of-hatch male broiler chicks were utilized in the study. Rations were fed ad libitum from date of chick arrival as follows: Starter—day 0 until day 14, grower day 14 to day 28, and finisher from day 28 to day 42 (the end date of the study). Coccidia vaccination for treatments in Groups 2 and 4 through 7.

| Treatment Group | Treatment | No. of Replicates | Cocci Vaccine | Cocci Challenge | DOSAGE: STARTER DOT 0-14 | DOSAGE: GROWER DOT 14-35 | DOSAGE: FINISHER DOT 35-42 |
| --- | --- | --- | --- | --- | --- | --- | --- |
| 1 | No feed additive | 12 | No | Yes | — | — | — |
| 2 | Vaccine control | 12 | Yes | Yes | — | — | — |
| 3 | No feed additive | 12 | No | No | — | — | — |
| 4 | Vaccine + inventive compound | 12 | Yes | Yes | 1.0 pound/ton | 2.0 pound/ton | 0.5 pound/ton |
| 5 | Vaccine + inventive compound | 12 | Yes | Yes | 1.0 pound/ton | 1.0 pound/ton | 0.5 pound/ton |
| 6 | Vaccine + inventive compound | 12 | Yes | Yes | 0.0 pound/ton | 1.5 pound/ton | 0.0 pound/ton |
| 7 | Vaccine + inventive compound | 12 | Yes | Yes | 1.0 pound/ton | 1.0 pound/ton | 0.0 pound/ton |

Two thousand one hundred birds (2,100) were assigned to seven (7) treatment groups with twelve (12) replicate pens per treatment and 25 birds per pen. The study began when birds are placed (day-of-hatch; DOT 0), at which time birds were allocated to experimental pens. Only healthy birds were selected. On DOT 0, group body weights were recorded by pen. No birds were replaced during the course of the study.

Analysis Methodology-Second Study

Birds received treatment appropriate feed from DOT 0 to DOT 42. All birds were weighed by pen on DOT 0, 13, 28, and 42. Feed added to each pen's feeder was weighed at the beginning of each formulation period on DOT 0 (starter), 13 (grower), and 28 (finisher). Any additional bags of feed were weighed (and documented) for each pen (as required) during each formulation period. Feed was distributed as needed to feeders from pre-weighed bags (assigned to each pen) throughout each period. Feed remaining in feeders (and feed bags if applicable) was weighed and disposed of on DOT 13, 28, and 42. Empty pan feeder weights were recorded prior to study initiation. The trial was terminated on DOT 42.

On Day 21 of the study, all birds except the negative control group received a coccidial inoculum containing: 100,000 oocysts per bird of *E. acervulina;* 50,000 oocysts per bird of *E. maxima;* and 75,000 oocysts per bird of *E. tenella.* The inoculum was mixed onto the feed found in the base of each pen's tube feeder.

On Day 26, three birds from each pen were selected, sacrificed, weighed, and examined for the degree of presence of coccidia lesions. The Johnson and Reid (1970) method of coccidiosis lesion scoring was used to score the infected region(s) of the intestine. The scoring was based on a 0 to 4 score, with 0 being normal and 4 being the most severe.

Also on Day 26, fresh fecal samples were collected from each pen. These representative samples were tested to determine the degree of oocysts shedding/cycling. Oocysts per gram were determined for each sample.

TABLE 6

| | Day 0 to 13 Performance Results | | | |
| --- | --- | --- | --- | --- |
| Treatment | Feed Intake | Adjusted FCR* | Non-Adjusted FCR | Weight Gain (kg) |
| 1. No Feed Additive - Cocci Challenge | 10.08A | 1.29AB | 1.31AB | 0.3245BC |
| 2. Vaccine Control | 10.05A | 1.29AB | 1.30AB | 0.3197CD |
| 3. No Feed Additive - No Cocci Challenge | 10.18A | 1.24BC | 1.25BC | 0.3321AB |
| 4. Vaccine + Zivo (1/2/0.5 pound/ton) | 10.04A | 1.32A | 1.33A | 0.3135D |
| 5. Vaccine + Zivo (1/1/0.5 pound/ton) | 9.82A | 1.26ABC | 1.27ABC | 0.3181CD |
| 6. Vaccine + Zivo (0/1.5/0 pound/ton) | 10.08A | 1.22C | 1.23C | 0.3362A |
| 7. Vaccine + Zivo (1/1/0 pound/ton) | 9.80A | 1.24BC | 1.26BC | 0.3245BC |

*FCR adjusted for mortality

TABLE 7

| | Day 0 to 28 Performance Results | | | |
| --- | --- | --- | --- | --- |
| Treatment | Feed Intake | Adjusted FCR* | Non-Adjusted FCR | Weight Gain (kg) |
| 1. No Feed Additive - Cocci Challenge | 40.26BC | 1.51A | 1.55A | 1.12D |
| 2. Vaccine Control | 39.70BC | 1.45BC | 1.50ABC | 1.20BC |
| 3. No Feed Additive - No Cocci Challenge | 43.43A | 1.41D | 1.45C | 1.27A |
| 4. Vaccine + Zivo (1/2/0.5 pound/ton) | 39.80BC | 1.47B | 1.51ABC | 1.18C |
| 5. Vaccine + Zivo (1/1/0.5 pound/ton) | 40.45AB | 1.45BCD | 1.50ABC | 1.21BC |
| 6. Vaccine + Zivo (0/1.5/0 pound/ton) | 41.28AB | 1.42CD | 1.46BC | 1.24AB |
| 7. Vaccine + Zivo (1/1/0 pound/ton) | 37.39C | 1.43BCD | 1.53AB | 1.21BC |

*FCR adjusted for mortality

TABLE 8

| | Day 0 to 42 Performance Results | | | | | | |
| --- | --- | --- | --- | --- | --- | --- | --- |
| Treatment | Feed Intake | Adjusted FCR* | Non-Adjusted FCR | Weight Gain | Percent Mortality | NE Percent Mortality | Cocci Percent Mortality |
| 1. No Feed Additive - Cocci Challenge | 84.72AB | 1.65A | 1.69A | 2.37C | 8.67B | 1.00B | 0.67C |
| 2. Vaccine Control | 83.18ABC | 1.63A | 1.70A | 2.49A | 14.33AB | 2.67AB | 5.33AB |
| 3. No Feed Additive - No Cocci Challenge | 87.88A | 1.55A | 1.58A | 2.54A | 6.00B | 1.33B | 0.33C |
| 4. Vaccine + Zivo (1/2/0.5 pound/ton) | 80.13BC | 1.59A | 1.64A | 2.41BC | 12.67AB | 3.33AB | 2.33BC |
| 5. Vaccine + Zivo (1/1/0.5 pound/ton) | 82.55ABC | 1.58A | 1.61A | 2.48A | 10.00B | 2.00AB | 4.00ABC |
| 6. Vaccine + Zivo (0/1.5/0 pound/ton) | 85.88AB | 1.60A | 1.64A | 2.52A | 9.67B | 2.00AB | 2.67BC |
| 7. Vaccine + Zivo (1/1/0 pound/ton) | 77.09C | 1.60A | 1.68A | 2.51A | 18.67A | 4.67A | 7.00A |

*FCR adjusted for mortality

TABLE 9

Mean Coccidia Lesion Scores

| Treatment | E. acervulina | E. maxima | E. tenella | Average |
|---|---|---|---|---|
| 1. No Feed Additive - Cocci Challenge | 1.81A | 2.50A | 1.56A | 1.95A |
| 2. Vaccine Control | 0.86B | 1.33BC | 1.22AB | 1.14B |
| 3. No Feed Additive - No Cocci Challenge | 1.11B | 1.11BC | 0.64C | 0.95B |
| 4. Vaccine + Zivo (1/2/0.5 pound/ton) | 1.03B | 1.25BC | 1.03BC | 1.10B |
| 5. Vaccine + Zivo (1/1/0.5 pound/ton) | 0.86B | 1.03C | 1.08B | 0.99B |
| 6. Vaccine + Zivo (0/1.5/0 pound/ton) | 1.11B | 1.39BC | 1.14AB | 1.21B |
| 7. Vaccine + Zivo (1/1/0 pound/ton) | 1.14B | 1.69B | 1.17AB | 1.33B |

Results—Second Study

This study compared the inventive product with and without a live coccidia vaccine in broilers challenged at 21 days of age with *Eimeria acervulina, E. maxima*, and *E. tenella*. It should be noted that there was not a designed *Clostridium perfringens* challenge. However, due to cleaning prior to this study with a pressure washer, the hardy *C. perfringens* spores were still present resulting in a mild N.E. in the study.

At 13 days, effects of the coccidia vaccine cycling can be observed (Table 6). By day 28, the coccidia challenge has peaked and begun to significantly affect performance. Treatments with the inventive composition in the grower had nearly the same FCR as the no challenge control (Table 7). Treatments with the inventive composition in the grower also had the heaviest body weight of the challenged treatments except the 2.0 pound/ton in grower.

By 42 days, compensatory growth resulted in less significant feed conversion differences (Table 8). Treatments with the inventive composition in the starter and grower plus the 1.5 pound in the grower only had the heaviest body weights. These were nearly the same as the not challenged control. Necrotic enteritis occurred at the peak of coccidia vaccine cycling and was found in all treatments, including those with no vaccine. Treatments using the inventive composition appeared to reduce the N.E. except the treatment containing two pounds in the grower.

Figure 10:
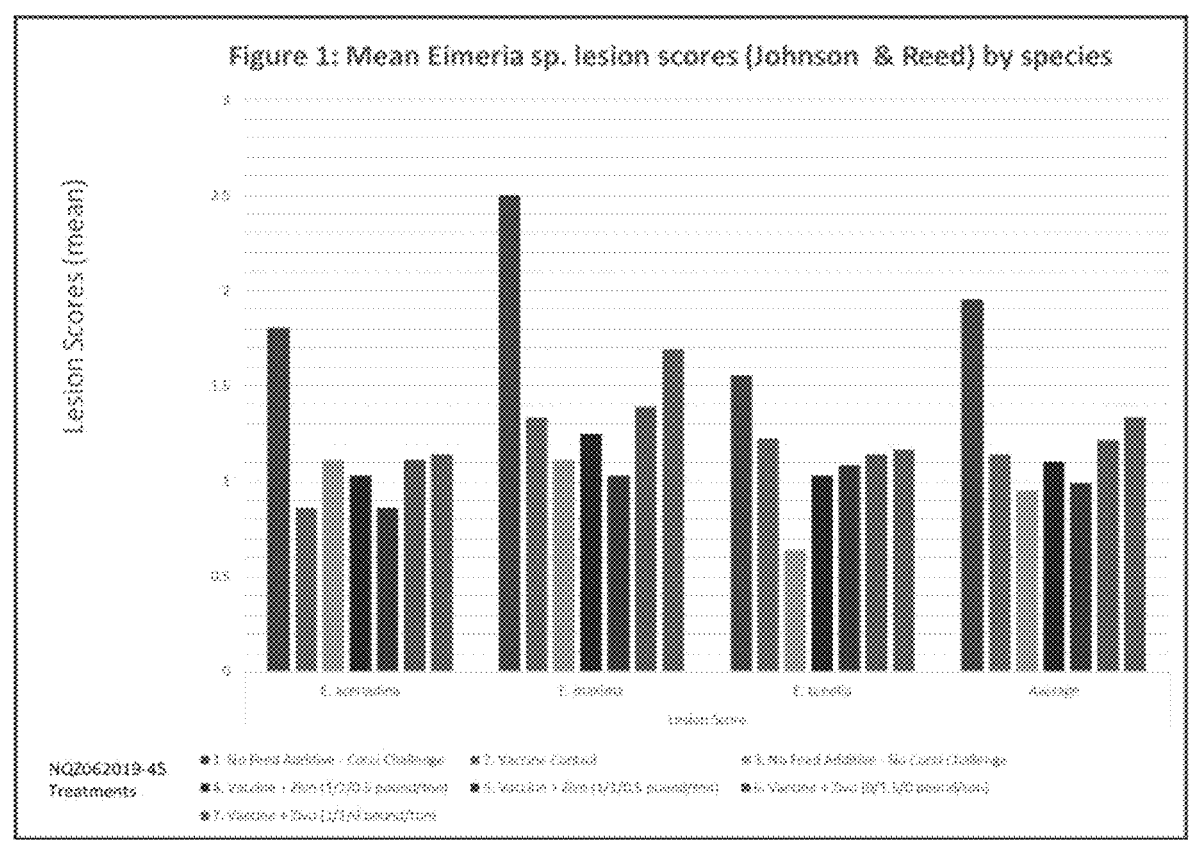
Figure 11:
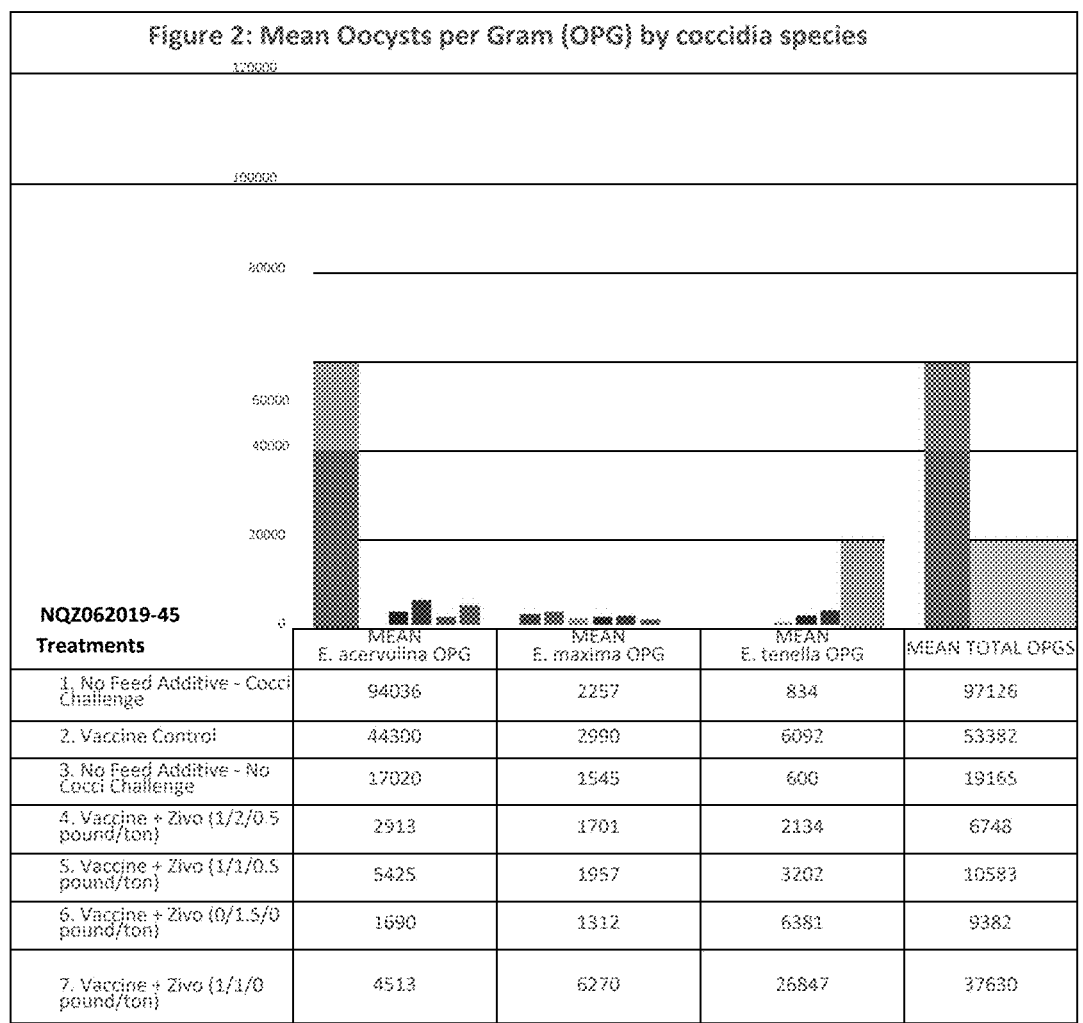

Five days post coccidia challenge, three birds per pen were lesion scored for *E. acervulina, E. maxima*, and *E. tenella*. All treatments lowered overall coccidia lesion scores (Table 9). This is readily observed in FIG. 10. At the peak of coccidia cycling, day 27, feces collected from each pen had oocyst counts per gram for each of the three challenge species of *Eimeria*. All treatments were very effective in lowering the oocysts/gram for all species as shown in FIG. 11. This is especially observed with *E. maxima*.

Third Study

Rations consisted of non-medicated commercial-type broiler starter, grower, and finisher diets compounded according to NRC guidelines and contain feedstuffs commonly used in the United States. Day-of-hatch male broiler chicks were utilized in the study. Rations were fed ad libitum from date of chick arrival as follows: Starter—day 0 until day 14, grower day 14 to day 28, and finisher from day 28 to day 42 (the end date of the study). Coccidia vaccination for treatments 4 and 5 only.

| # TREATMENT | REPS | COCCI VACCINE | CHALLENGE | DOSAGE-STARTER DOT 0-14 | DOSAGE-GROWER DOT 14-28 | DOSAGE-FINISHER DOT 28-42 |
|---|---|---|---|---|---|---|
| 1 No Feed Additive | 12 | No | No | — | — | — |
| 2 No Feed Additive | 12 | No | Yes | — | — | — |
| 3 Salinomycin | 12 | No | Yes | 60 g/ton | 60 g/ton | 60 g/ton |
| 4 Vaccine Control | 12 | Yes | Yes | — | — | — |
| 5 Disclosed Inventive Compound | 12 | Yes | Yes | 1.0 lb/ton | 1.0 lb/ton | 0.5 lb/ton |

One thousand five hundred birds (1,500) were randomly assigned to 5 treatment groups with 12 replicate pens per treatment and 25 birds per pen. The study began when birds were placed (day-of-hatch; DAY 0), at which time birds were allocated to experimental pens. On day 0, group body weights were recorded by pen. No birds were replaced during the course of the study.

Analysis Methodology—Third Study

All birds were weighed by pen on days 0, 14, 28, and 42. Feed added to each pen's feeder was weighed at the beginning of each formulation period on day 0 (starter), day 14 (grower), and day 28 (finisher). Feed was distributed as needed to feeders from pre-weighed bags assigned to each pen throughout each period. Feed remaining in feeders was weighed and disposed of on days 14, 28, and 42. The trial was terminated on day 42.

On day 21 of the study, all birds except the negative control group received a coccidial inoculum containing: 100,000 oocysts per bird of *E. acervuline,* 50,000 oocysts per bird of *E. maxima*, and 75,000 oocysts per bird of *E. tenella*.

On Day 26, three birds from each pen were selected, sacrificed, weighed, and examined for the degree of presence of coccidia lesions. Scoring was based on a 0 to 4 score, with 0 being normal and 4 being the most severe.

On Day 26, fresh fecal samples were collected from each pen. These representative samples were tested to determine the degree of oocysts shedding/cycling. Oocysts per gram were determined for each sample.

TABLE 10

Day 0 to 14 Performance Results

| Treatment** | Feed Intake | Adjusted FCR* | Non-Adjusted FCR | Weight Gain (kg) |
|---|---|---|---|---|
| 1. No Feed Additive - No Vacc, No Challenge | 11.80A | 1.32B | 1.32B | 0.36A |
| 2. No Feed Additive - No Vacc, Challenge | 11.67A | 1.33AB | 1.33AB | 0.35AB |
| 3. Salinomycin (60 g/ton) - No Vacc, Challenge | 12.09A | 1.41A | 1.42A | 0.34B |
| 4. Vaccine Control - Vacc, Challenge | 11.66A | 1.39AB | 1.39AB | 0.34B |
| 5. Disclosed compound - Vacc, Challenge | 11.57A | 1.36AB | 1.36AB | 0.34B |

*FCR adjusted for mortality
**Gray color denotes vaccinated treatments

TABLE 11

Day 0 to 28 Performance Results

| Treatment** | Feed Intake | Adjusted FCR* | Non-Adjusted FCR | Weight Gain (kg) |
|---|---|---|---|---|
| 1. No Feed Additive - No Vacc, No Challenge | 46.40A | 1.44C | 1.44C | 1.31A |
| 2. No Feed Additive - No Vacc, Challenge | 43.95B | 1.52A | 1.53AB | 1.15C |
| 3. Salinomycin (60 g/ton) - No Vacc, Challenge | 44.75B | 1.50AB | 1.51B | 1.20B |
| 4. Vaccine Control - Vacc, Challenge | 44.56B | 1.53A | 1.57A | 1.19B |
| 5. Disclosed compound - Vacc, Challenge | 43.69B | 1.49B | 1.51B | 1.19B |

*FCR adjusted for mortality
**Gray color denotes vaccinated treatments

TABLE 12

Day 0 to 41 Performance Results

| Treatment** | Feed Intake | Adjusted FCR* | Non-Adjusted FCR | Weight Gain (kg) | Percent Mortality | Cocci Percent Mortality |
|---|---|---|---|---|---|---|
| 1. No Feed Additive - No Vacc, No Challenge | 95.97A | 1.57C | 1.58C | 2.65A | 2.00AB | 0.00A |
| 2. No Feed Additive - No Vacc, Challenge | 92.13B | 1.64A | 1.65AB | 2.42C | 1.67AB | 0.00A |
| 3. Salinomycin (60 g/ton) - No Vacc, Challenge | 92.63B | 1.60AB | 1.61BC | 2.49BC | 1.33B | 0.00A |
| 4. Vaccine Control - Vacc, Challenge | 91.83B | 1.63A | 1.67A | 2.51B | 5.67A | 1.00A |
| 5. Disclosed compound - Vacc, Challenge | 92.15B | 1.59BC | 1.61BC | 2.52B | 2.67AB | 0.00A |

*FCR adjusted for mortality
**Gray color denotes vaccinated treatments

TABLE 13

Mean Coccidia Lesion Scores

| Treatment | E. acervulina | E. maxima | E. tenella | Average |
|---|---|---|---|---|
| 1. No Feed Additive - No Vacc, No Challenge | 1.36C | 1.17C | 0.67C | 1.07D |
| 2. No Feed Additive - No Vacc, Challenge | 2.20A | 1.97A | 2.45A | 2.20A |
| 3. Salinomycin (60 g/ton) - No Vacc, Challenge | 2.31A | 1.78AB | 2.03AB | 2.04AB |
| 4. Vaccine Control - Vacc, Challenge | 1.83B | 1.69AB | 1.86B | 1.80B |
| 5. Disclosed compound - Vacc, Challenge | 1.61BC | 1.42BC | 1.56B | 1.53C |

**Gray color denotes vaccinated treatments

TABLE 14

Results of Oocysts per gram (OPG) of Feces

| Treatment | OPG A | OPG M | OPG T | Total OPG |
|---|---|---|---|---|
| 1. No Feed Additive - No Vacc, No Challenge | 1,412B | 67A | 22A | 1,501B |
| 2. No Feed Additive - No Vacc, Challenge | 25,763A | 4,869A | 645A | 31,277AB |
| 3. Salinomycin (60 g/ton) - No Vacc, Challenge | 23,995A | 9,666A | 21,455A | 55,117A |

TABLE 14-continued

| | | | | Total |
|---|---|---|---|---|
| Treatment | OPG A | OPG M | OPG T | OPG |
| 4. Vaccine Control - Vacc, Challenge | 7,165B | 6,831A | 4,602A | 18,598B |
| 5. Disclosed compound - Vacc, Challenge | 5,436B | 2,557A | 917A | 8,910B |

Results of Oocysts per gram (OPG) of Feces

**Gray color denotes vaccinated treatments

Results—Third Study

Prior to the challenge at day 14, there were small differences in performance parameters (Table 10). At the peak of the challenge on day 28, birds treated using the vaccine plus the disclosed inventive compound had a body weight gain similar to salinomycin (Table 11). On day 28, it was found that those birds treated with the vaccine plus the disclosed inventive compound demonstrated lower non-adjusted FCR and adjusted FCR than the vaccine only treatment, and demonstrated similar FCR to birds treated with salinomycin (Table 12).

The overall average coccidia lesion scores six days post challenge demonstrated that vaccine plus the disclosed inventive compound had either numerically or statistically significant lower coccidia lesions than the groups receiving the vaccine only or the challenged no feed additive control (Table 13). The oocysts per gram (OPG) of feces gave a similar trend as the lesion scores (Table 14). The peak of the challenge which should be on the day of feces collection (day 27) found the challenge control, salinomycin, had the highest count of oocysts at this time. (This result also confirms the loss of ionophore effectiveness noted above.)

For the entire 41-day study period, the group receiving the vaccine plus the disclosed inventive anticoccidial compound had improved FCR over the vaccine alone group, and results similar to salinomycin (Table 3). The heaviest weight gain of any challenged group was observed in the group receiving the vaccine plus the disclosed inventive compound (2.52 kg$^B$). Only the birds not challenged were heavier at 2.65 kg$^A$. The highest mortality (5.67%$^A$) was in the vaccine only treatment and the lowest in the salinomycin only (1.33%$^B$). It was found that the combination of the vaccine and the disclosed inventive compound had similar overall mortality to salinomycin (Table 12).

We claim:

1. A method for preventing coccidiosis in a broiler chicken, comprising the steps of:
   selecting a vaccine dose containing between 200 and 3000 sporulated oocysts;
   mixing the vaccine with water at a dosage of 240 ml of water per 1,000 doses to form a vaccine-water combination;
   spraying a one-day old broiler chicken with a dose of the vaccine-water combination;

forming a lipopolysaccharide/Lipid A treatment compound produced by a gram negative bacteria selected from the group consisting of *Variovorax paradoxus* and *Rhodobacter sphaeroides*, the treatment compound having a neutral effect on pathogens, the compound including an active fraction, the compound being formed through the extraction of freeze-dried bacteria and collecting the water layer for freeze-drying, resolubilizing the freeze-dried fraction in water, ultrafiltering the solubilized fraction to remove low molecular weight substances and salts, and affinity purifying the high-molecular weight fraction from which the active fraction is eluted; and
administering an effective amount of the treatment compound in combination with drink or feed to a broiler chicken in vivo to enhance the effectiveness of the vaccine,
whereby the lipopolysaccharide/Lipid A treatment compound modulates TLR4 activity with a downstream effect being enhancement of the innate and adaptive immune processes of the vaccinated broiler chicken.

2. The method of claim 1, wherein the treatment compound is an algal composition.

3. The method of claim 1, wherein the treatment mixture is administered to the broiler chicken at different stages of development.

4. The method of claim 1, wherein the different stages of development include the starter stage of 0-21 days, the grower stage of 22-35 days, and the finisher stage of 36-42 days.

5. The method of claim 4, wherein the compound is administered in the amount of between 0.0 pound per ton of feed and 1.0 pound per ton of finished feed at the starter stage.

6. The method of claim 4, wherein the compound is administered in the amount of between 1.0 pound per ton of feed and 2.0 pounds per ton of finished feed at the grower stage.

7. The method of claim 4, wherein the compound is administered in the amount of between 0.0 pound per ton of feed and 1.0 pound per ton of finished feed at the finisher stage.

* * * * *